US009981897B2

(12) United States Patent
Pelzer et al.

(10) Patent No.: US 9,981,897 B2
(45) Date of Patent: May 29, 2018

(54) ETHERS OF BIS(HYDROXYMETHYL)CYCLOHEXANES

(71) Applicant: BASF SE, Ludwigshafen (DE)

(72) Inventors: Ralf Pelzer, Fürstenberg (DE); Roland Merten, Ludwigshafen (DE); Pierre Fournier, Karlsruhe (DE); Markus C. Biel, Mannheim (DE)

(73) Assignee: BASF SE (DE)

( * ) Notice: Subject to any disclaimer, the term of this patent is extended or adjusted under 35 U.S.C. 154(b) by 0 days. days.

(21) Appl. No.: 15/211,247

(22) Filed: Jul. 15, 2016

(65) Prior Publication Data
US 2016/0347698 A1 Dec. 1, 2016

Related U.S. Application Data

(62) Division of application No. 14/129,715, filed as application No. PCT/EP2012/062546 on Jun. 28, 2012, now Pat. No. 9,452,962.

(60) Provisional application No. 61/658,937, filed on Jun. 13, 2012, provisional application No. 61/551,949, filed on Oct. 27, 2011, provisional application No. 61/504,246, filed on Jul. 4, 2011.

(30) Foreign Application Priority Data

Jul. 1, 2011 (EP) ..................................... 11172390

(51) Int. Cl.
C07C 43/115 (2006.01)
C07C 29/44 (2006.01)
C07C 41/01 (2006.01)
C07C 41/16 (2006.01)
C11B 9/00 (2006.01)
C07C 41/20 (2006.01)
C07C 43/162 (2006.01)
C07C 43/178 (2006.01)
C07C 41/08 (2006.01)
A23L 27/20 (2016.01)

(52) U.S. Cl.
CPC .......... C07C 43/115 (2013.01); A23L 27/203 (2016.08); C07C 29/44 (2013.01); C07C 41/01 (2013.01); C07C 41/08 (2013.01); C07C 41/16 (2013.01); C07C 41/20 (2013.01); C07C 43/162 (2013.01); C07C 43/1781 (2013.01); C11B 9/0034 (2013.01); C07C 2601/14 (2017.05)

(58) Field of Classification Search
None
See application file for complete search history.

(56) References Cited

U.S. PATENT DOCUMENTS

| 3,236,900 A | 2/1966 | McConnell et al. |
| 4,751,273 A | 6/1988 | Lapin et al. |
| 4,775,732 A | 10/1988 | Lapin |
| 4,999,090 A | 3/1991 | Tateno et al. |
| 5,183,946 A | 2/1993 | Liu et al. |

FOREIGN PATENT DOCUMENTS

| EP | 538681 A1 | 4/1993 |
| EP | 538685 A2 | 4/1993 |
| JP | S63-167357 A | 7/1988 |
| JP | H10-310605 | 11/1998 |
| JP | H11-029512 A | 2/1999 |
| JP | H11-035969 A | 2/1999 |
| JP | H11-071311 A | 3/1999 |
| JP | H11-071312 A | 3/1999 |
| WO | WO-90/09364 A1 | 8/1990 |
| WO | WO-2007092071 A1 | 8/2007 |
| WO | WO-2011139360 A1 | 11/2011 |
| WO | WO-2011139361 A1 | 11/2011 |

OTHER PUBLICATIONS

Database CAPLUS in STN, Acc. No. 1998:758654, Mihira et al., JP 10310605 A (Nov. 24, 1998) (abstract).*
Tindall, G.W. et al., "Bonded Cyclodestrin Stationary Phase Columns for the Separation of Cis/Trans Cyclohexane Derivatices", Journal of Liquid Chromatography, 1987, vol. 10, No. 6, pp. 1077-1084.
Database Registry (Online), Chemical Abstracts Service, Columbus, OH, Database Accession No. 54889-63-3, dated Nov. 16, 1984.
Deagostino, A., et al., "Intramolecular Diels-Alder reaction of functionalized trienes: synthesis of medium-ring lactones", Journal of the Chemistry Society, Perkin Transactions 1, No. 5, (1998), pp. 881-888.
Etsuno, J., et al., "New 4-alkoxy-methyl:cyclohexyl methanol(s) and preparation—used as fragrance for soaps, shampoos, hair rinses, detergents, cosmetics, spays, and aromatics", Database WPI Accession No. 1999-175609, XP-002662919, dated Feb. 2, 1999.
Etsuno, J., et al., "Novel cyclohexylakanol—for perfume composition", Thomson Scientific, Database WPI Accession No. 1999-248461, XP-002662920, dated Mar. 16, 1999.
Etsuno, J., et al., "Perfume composition—contains 4-alkoxy-methyl cyclo-hexyl methanol", Database WPI Accession No. 1999-186609, XP-002662918, dated Feb. 9, 1999.
Guy, R., et al., "A Facile One-Pot Synthesis of Symmetrical and Unsymmetrical Acetaldehyde Acetals From Primary Alcohols", Synthetic Communications, vol. 22, No. 5, (1992), pp. 687-692.
Haggis, G., et al., "Alicyclic Glycols. Part VIII 1:2-Bishydroxymethyl-cyclohexane", Journal of the Chemical Society, vol. 79, (1953), pp. 389-398.
International Report on Patentability for PCT/EP2012/062546, dated Jan. 7, 2014.
International Search Report for PCT/EP2012/062546 dated Jan. 2, 2013.

(Continued)

Primary Examiner — Brian J Davis
(74) Attorney, Agent, or Firm — Drinker Biddle & Reath LLP

(57) ABSTRACT

The present invention relates to ethers of 1,2-, 1,3- and 1,4-bis(hydroxymethyl)cyclohexanes, to the preparation of such ethers and also to the use of such ethers as fragrances and as formulation auxiliaries in fragrance-comprising preparations.

35 Claims, No Drawings

(56) References Cited

OTHER PUBLICATIONS

McDonald, F., et al., "Method 5: Synthesis of Alkyl Ethers from Vinylic Ethers", Science of Synthesis, 2008, vol. 37, pp. 197-205.
Solladie, G., et al., "A New Class of Chiral Smectic Liquid Crystals: Substituted Biphenylylcyclohexylideneethanones Having and Axial Chirality", Journal of Organic Chemistry, vol. 50, No. 21, (1985), pp. 4062-4068.
Van Bebber, J., et al., "Efficient Desymmetrization of meso-cis-1,2-Cyclohexanedimethanol with Differentiation between Diastereotopic and Enantiotopic C-H Bonds by (-)-Sparteine Mediated Deprotonation", Chem. Eur. J., vol. 5, No. 6, (1999), pp. 1905-1916.
Wolinsky, J., et al., "Reaction of Methylmagnesium Iodide and Diethy 1,2-Cyclohexanedicarboxylates", Journal of Organic Chemistry, vol. 33, No. 10, (1968), pp. 3950-3953.
Yadav, J., et a., "A Novel Approach Towards the Synthesis of Functionalized Taxane Skeleton Emloying Wittig Rearrangement", Tetrahedron Letters, vol. 32, No. 23, (1991), pp. 2629-2632.
Database CAPLUS in STN, Accession No. 1968:505971, Wolinsky et al., Journal of Organic Chemistry 33(10), pp. 3950-3953 (abstract) 1968.

\* cited by examiner

ETHERS OF BIS(HYDROXYMETHYL)CYCLOHEXANES

RELATED APPLICATIONS

This application is a divisional application of U.S. patent application Ser. No. 14/129,715, filed Dec. 27, 2013, which is a national stage application (under 35 USC § 371) of PCT/EP2012/062546, filed Jun. 28, 2012 and which is incorporated by reference herein in its entirety. This application also claims the benefit of U.S. Provisional Application No. 61/658,937, filed Jun. 13, 2012; U.S. Provisional Application No. 61/551,949, filed Oct. 27, 2011; U.S. Provisional Application No. 61/504,246, filed Jul. 4, 2011; and European Application No. 11172390.4, filed Jul. 1, 2011, all of which are incorporated by reference herein in their entirety.

The present invention discloses ethers of 1,2-, 1,3- and 1,4-bis(hydroxymethyl)cyclohexanes, the preparation of such ethers, and the use of such ethers as fragrance and as formulation auxiliary in fragrance-comprising preparations.

Derivatives of 1,2-, 1,3- and 1,4-bis(hydroxymethyl)cyclohexane and their substituted derivatives with substituents on the cyclohexane ring and/or on the exocyclic methylene groups are of interest as ingredients in cosmetics, for example as fragrances or else as waxlike substances, or formulation auxiliaries, for example in cosmetic formulations.

Fragrances and formulation auxiliaries are of great interest especially in the field of cosmetics and also laundry and cleaning detergents. Fragrances of natural origin are mostly expensive, often limited in their available amount and, on account of fluctuations in environmental conditions, are also subject to variations in their content, purity etc. It is therefore of great interest to be able to replace, at least partially, fragrances of natural origin with synthetically obtainable substances. Often, in this connection, the natural substance is not replicated chemically, but chemically synthesized compounds are selected as substitutes for natural substances on account of their odor, where substitute and natural substance do not necessarily have to have a chemical-structural similarity.

However, since even small changes in chemical structure bring about massive changes in the sensory properties such as odor and also taste, the targeted search for substances with certain sensory properties such as a certain odor is extremely difficult. The search for new fragrances and flavorings is therefore in most cases difficult and laborious without knowing whether a substance with the desired odor and/or taste will even actually be found.

Suitable formulation auxiliaries, in particular those with good solvent properties, are likewise of great interest in the field of cosmetics and also of laundry and cleaning detergents. Particularly for odor-carrying compositions such as perfumes, substances are desired which have good solvent properties and a very low, or even no, toxicity.

Although individual syntheses, including the classic ether syntheses, are already known, the direct synthetic access without any, or without relatively large, quantities of by-products or salts, and also a very easy purification, however, have hitherto not been published. Easy purification to give pure and highly pure substances is, however, necessary for the desired applications since malodors can arise even as a result of the smallest amounts of other substances.

JP 11-035969 A discloses a perfume composition comprising 4-alkoxymethylcyclohexylmethanol compounds with a lily-of-the-valley-type odor, where the alkoxy radical can be C1- to C10-alkyl, C3- to C10-cycloalkyl or C2- to C10-alkenyl. As alkoxy radical, preferred structures have C1- to C5-alkyl, C3- to C5-cycloalkyl or C3- to C5-alkenyl. Particularly preferred radicals are methyl, ethyl, isopropyl and allyl. Also disclosed are preparation processes and also the use of the specified substances as flavorings/fragrances, especially in perfumes.

The diethers of 1,4-bis(hydroxymethyl)cyclohexane and the monoether 4-vinyloxymethylcyclohexylmethanol are not disclosed.

JP 11-029512 A discloses 4-alkoxymethylcyclohexylmethanol compounds with floral odor, where the alkoxy radical can be C2- to C10-alkyl, C3- to C10-cycloalkyl or C4- to C10-alkenyl. Preferred structures have, as alkoxy radical, C2- to C5-alkyl, C5- to C6-cycloalkyl or C4- to C5-alkenyl. Particularly preferred radicals are ethyl and isopropyl. Also disclosed are preparation processes and also the use of the specified substances as flavorings/fragrances, in particular in perfumes.

The diethers of 1,4-bis(hydroxymethyl)cyclohexane and the monoether 4-vinyloxymethylcyclohexylmethanol are not disclosed.

JP 11-071312 A discloses cyclohexylalkanols and perfume mixtures comprising these. These compounds have a floral, woody flavor note ("muguet fragrance") with long-lasting odiferous properties, which is said to make them particularly suitable as fragrance for example in perfumes, toiletries.

The compounds of the type 1-($CR_1R_2$—OH)-4-($CR_3R_4$—$OR_5$)-cyclohexane exhibit, as $R_1$ to $R_4$, identical or different radicals selected from C1- to C3-alkyl and hydrogen, where not all radicals $R_1$, $R_2$, $R_3$ and $R_4$ are hydrogen at the same time. $R_5$ is C1- to C3-alkyl.

The diethers of the type 1,4-bis(alkoxymethyl)cyclohexane, of the type 1-($CR_1R_2$—$OR_6$)-4-($CR_3R_4$—$OR_5$)-cyclohexane and the monoethers of the type 1-($CR_1R_2$—OH)-4-($CR_3R_4$—$OR_5$)-cyclohexane, where $R_5$ is selected from C4- to C6-alkyl, C3- to C6-cycloalkyl and C2- to C5-alkenyl, are not disclosed. 4-Vinyloxymethylcyclohexylmethanol is also not mentioned.

JP 11-071311 A discloses diethers of the type 1,4-bis(alkoxymethyl)cyclohexane, where the alkoxy radicals are selected from C14- to C30-alkyl. The substances are waxlike and in particular have no color and no odor at all, for which reason they are said to be particularly suitable for cosmetic formulations.

The diethers 1,4-bis(alkoxymethyl)cyclohexane with shorter radicals than C10 and also the monoether 4-vinyloxymethylcyclohexylmethanol are not disclosed.

JP S 63-167357 A discloses diethers of the type 1,4-bis(alkoxymethyl)cyclohexane, where the alkoxy radicals are C12-alkyl (experiment number "V-8"). All of the other disclosed substances are esters or diesters, no diethers.

A preparation process for monoethers is disclosed in EP 538681 A1: a monovinyl ether substrate is prepared from the reaction of the corresponding diol with the corresponding divinyl ether. The substrate comprises the two diol groups as substituents on a ring structure, which can inter alia have also a C3- to C10-cycloalkylene structure. Of the cyclohexanes, only 1,4-bis(hydroxymethyl)cyclohexane is specifically disclosed, although this is as one of the preferred substrates. According to the disclosure therein, the process is suitable for the preparation of the commercially desirable monoethers using commercially undesirable diethers, which arise as by-product in the preparation of the monoethers by the "Reppe vinylation" of the diol with ethyne in relatively small amounts of up to 20 percent fraction.

Ethers other than vinyl are not disclosed. The direct preparation of the pure monoethers and of the pure diethers is not disclosed.

A preparation process for vinyloxy-hydroxyalkylcycloalkanes (i.e. monovinyl ethers of bis(hydroxyalkyl)cycloalkanes) is disclosed in WO 90/09364. The preparation takes place by alkenylation of the alcohol function of the corresponding diols with ethyne. Only the compound 1,4-bis(hydroxymethyl)cyclohexane is specifically disclosed as cyclohexane substrate to be alkenylated. Molten potassium hydroxide is used as reagent. The preparation of the monovinyl ether of 1,4-bis(hydroxymethyl)cyclohexane is disclosed. According to this disclosure, the monovinyl ether is particularly preferred as reactive crosslinker for polyurethanes since the vinyl function can be polymerized into a precursor molecule by radical means, whereas the alcohol function then takes on the crosslinking during the polyurethane formation.

U.S. Pat. No. 5,183,946 is a continuation-in-part of two priority applications which led to the above-cited WO90/09364. It more precisely specifies the preference for C6 rings as nucleus of the substrates. The monovinyl ether and the divinyl ether of 1,4-bis(hydroxymethyl)cyclohexane are specifically disclosed, the ethers always occurring only in the mixture of the three constituents monoether, diether and diol. The cis/trans isomerism is mentioned in the case of the monovinyl ether of 1,4-bis(hydroxymethyl)cyclohexane and determines the fractions of cis and trans form present.

As in WO90/09364, the ethers are useful crosslinkers for polyurethane polymers.

U.S. Pat. No. 4,751,273 discloses the preparation of mixtures of mono- and divinyl ethers from a diol by vinylation by means of ethyne and potassium hydroxide ("Reppe vinylation"). According to the disclosure, diethers and monoethers could be separated by distillation if desired. Specified as suitable diol is, besides others, also 1,4-bis(hydroxymethyl)cyclohexane. The ethers can be reacted as single substances following separation and—preferably—directly as reaction mixture with isocyanates to give crosslinking reactive monomer mixtures for the polyurethane preparation.

U.S. Pat. No. 4,775,732 discloses vinyl-ether-terminated esters and urethane oligomers for polyurethane preparation. These are prepared from vinyl ethers, which for their part are prepared from the alkenylation of diols such as bis(hydroxyalkyl)cycloalkanes with a ring size from 5 to 8, such as, for example, a 6-membered ring. Although, according to this disclosure, it is in principle possible to prepare the monoether in pure form, it is more probable—according to the disclosure—however to obtain a mixture of monoether and diether. However, this mixture can be purified if desired. Preferred substrates are bis(hydroxyalkyl)cyclohexanes on account of their ready availability. Of suitability is, inter alia, 1,4-bis(hydroxyalkyl)cyclohexane, where other substitution patterns could in principle be used where, according to the disclosure, the same results do not necessarily have to be achievable. Particular preference is given to 1,4-bis(hydroxymethyl)cyclohexane as substrate.

The preparation of ethers is known in principle to the person skilled in the art. Thus, for example, preparation procedures for ether synthesis have been published and referenced in JP 11-035969 A, JP 11-029512 A, JP 11-071312 A and JP 11-071311 A. Further ether syntheses from the parent alcohols are likewise known in general to the person skilled in the art, for example Williamson syntheses, and also customary metal-catalyzed and metal-mediated reactions of organic chemistry.

It was an object of the present invention to find novel bis(hydroxymethyl)cyclohexanes. It was a further object to find novel fragrances. In particular, odor-intensive substances were sought. Preference was given in particular to those substances with fruity notes. Also sought were novel preparation procedures which produce the desired substances directly and while minimizing the amount and number of secondary components and also with simplification of the purification.

Substances selected from mono- and diethers of cis- and/or trans-1,2-, 1,3- and 1,4-bis(hydroxymethyl)cyclohexane, their derivatives alkyl-substituted on the cyclohexane ring and/or on the exocyclic methylene groups, and also their mixtures, their preparation and their use as fragrances and flavorings, and also as formulation auxiliaries for fragrance-comprising preparations, have been found.

A preparation process has also been found for the preparation of such mono- and diethers of cyclohexane derivatives, characterized by the step of alkenylating alcohol groups in alcohol-group-bearing cyclohexane derivatives with alkynes to give alkenyl ether groups.

A preparation process has also been found for the preparation of such mono- and diethers of cyclohexane derivatives, characterized by the step of reducing alkenyl ether groups in monoalkenyl and dialkenyl ethers of cyclohexane derivatives with hydrogen in the presence of a catalyst based on transition metals to give the corresponding alkyl ethers.

It has likewise been found that the two variants of the preparation process according to the invention by means of alkenylation and reduction combined with one another makes possible the provision of alkyl ethers by firstly, in a first step, the alkenylation of alcohol groups in alcohol-group-carrying cyclohexane derivatives taking place with alkynes to give alkenyl ether groups, and in a second, subsequent step, the reduction of these alkenyl ether groups taking place to give the corresponding alkyl ether groups.

This second step can also take place without prior purification of the first reaction step. Thus, the two reactions can be carried out directly in succession, for example in the same reaction container or in directly successive containers, in which case a purification may take place in between, but does not have to.

There have been found cyclohexane derivatives with a structure according to formula 1a, 1b or 1c (formula 1a, 1b, 1c)

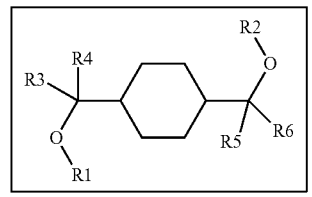

1a

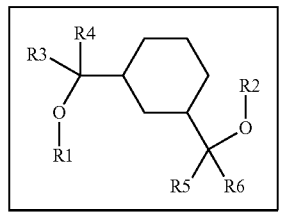

1b

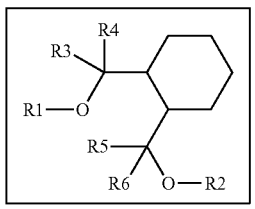

where the substituents on the cyclohexyl ring may be in cis or trans position to one another, and
a) for formula 1a
R3 to R6 are hydrogen and R1 and R2 independently of one another are selected from the group consisting of C2- to C6-alkyl, C5-alkenyl, C3- to C6-cycloalkenyl and C3- to C6-cycloalkyl, more particularly from the group consisting of C3-alkyl, C6-alkyl, C5-alkenyl, C3- to C6-cycloalkenyl and C3- to C6-cycloalkyl, or
at least one radical from R3 to R6 is not methyl or hydrogen, and the other radicals R3 to R6 independently of one another are selected from the group consisting of C1- to C6-alkyl, C3- to C6-cycloalkyl, C3- to C6-cycloalkenyl, C2- to C6-alkenyl and hydrogen, and R1 and R2 independently of one another are selected from the group consisting of C1- to C6-alkyl, C2 to C5-alkenyl, C3- to C6-cycloalkenyl and C3- to C6-cycloalkyl, or
at least one radical from R1 and R2 is not methyl or ethyl, R3 and R4 are methyl, R5 and R6 are hydrogen, and also R1 and R2 independently of one another are selected from the group consisting of C1- to C6-alkyl, C3- to C6-cycloalkyl, C3- to C6-cycloalkenyl, C2- to C6-alkenyl, or
R1 and R2 independently of one another are selected from the group consisting of C1- to C6-alkyl, C3- to C6-cycloalkyl, C3- to C6-cycloalkenyl, C2- to C6-alkenyl, and at least one radical from R3 to R6 is not hydrogen,
with the exception of compounds of the formula 1a in which R1 and R2 are methyl or ethyl and at the same time R3 and R4 are each methyl and R5 and R6 are each hydrogen,
b) for formula 1b
R1 to R6 independently of one another are selected from the group consisting of C1- to C6-alkyl, C3- to C6-cycloalkyl, C3- to C6-cycloalkenyl, C2- to C6-alkenyl and hydrogen,
where at least one radical from R1 and R2 in formula 1b is not hydrogen,
c) for formula 1c
R1 to R6 independently of one another are selected from the group consisting of C2- to C6-alkyl, C3- to C6-cycloalkyl, C3- to C6-cycloalkenyl, C2- to C6-alkenyl and hydrogen, and R1 and R2 are not hydrogen, or
R1 to R6 independently of one another are selected from the group consisting of C1- to C6-alkyl, C3- to C6-cycloalkyl, C3- to C6-cycloalkenyl, C2- to C6-alkenyl and hydrogen,
where those compounds of formula 1c are excluded for which R1 is hydrogen and R2 at the same time is methyl, C4-alkyl or vinyl,
with the proviso that the summed total number of the carbon atoms in all radicals R1 to R6 for formulae 1a, 1b and 1c is in each case only a whole numerical value from 2 to 20.

C1- to C6-Alkyl in the context of this invention comprises structural units such as methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

C3- to C6-Cycloalkyl in the context of this invention comprises structural units such as cyclopropyl, cyclobutyl, cyclopentyl and cyclohexyl.

C3- to C6-Cycloalkenyl in the context of this invention comprises structural units such as $C_5$-$C_8$-cycloalkenyl such as cycloprop-1-enyl, cyclobut-1-enyl, cyclopent-1-enyl, cyclopent-2-enyl, cyclopent-3-enyl, cyclohex-1-enyl, cyclohex-2-enyl and cyclohex-3-enyl.

C2- to C6-Alkenyl in the context of this invention comprises structural units such as ethenyl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl.

Subgroups selected from these groups include, of course, the structural units having the selected number of carbon atoms. Accordingly "C2- to C3-alkyl" comprises the structural units having 2 and 3 carbon atoms, i.e. ethyl, n-propyl and 1-methylethyl.

Preferred cyclohexane derivatives of the formulae 1a, 1b and 1c, as the total number of the carbon atoms in radicals R1 to R6, have a numerical value of not more than 15, more preferably not more than 12, very preferably not more than 8, and more particularly not more than 6.

Additionally preferred are cyclohexane derivatives of the formulae 1a, 1b and 1c in which R1 and R2 are not hydrogen (diethers).

Additionally preferred are cyclohexane derivatives of the formulae 1a, 1b and 1c which are enriched in terms of the cis isomer or the trans isomer. Preference is given more particularly to cyclohexane derivatives of the formulae 1a, 1b and 1c which are enriched in terms of the cis isomer or the trans isomer and whose cis/trans ratio, i.e. the ratio by mass or by moles of cis isomer to trans isomer, has a value of 60:40 and more particularly at least 70:30. Likewise preferred are cyclohexane derivatives of the formulae 1a, 1b and 1c in which the trans/cis ratio, i.e. the ratio by mass or by moles of trans isomer to cis isomer, has a value of at least 60:40 and more particularly at least 70:30. Particularly preferred are cyclohexane derivatives of the formulae 1a, 1b and 1c having a cis/trans ratio or those having a trans/cis ratio of at least 80:20, very preferably of at least 90:10 and more particularly of at least 95:5, such as, for example, 98:2, 99:1 or 99.9:0.1 or higher. Especially preferred are cyclohexane derivatives of the formulae 1a, 1b and 1c having a cis/trans ratio or those having a trans/cis ratio of at least 99:1.

Further preferred are cyclohexane derivatives of the formulae 1a, 1b and 1c where R1 is the same as R2.

Further preferred are also cyclohexane derivatives of the formulae 1a, 1b and 1c where R1 to R4 are methyl, and more particularly those in which R5 and R6 are hydrogen.

Further preferred are also cyclohexane derivatives of the formulae 1a, 1b and 1c in which R3, R4, R5 and R6 are selected from hydrogen and methyl, and more particularly those in which R3, R4, R5 and R6 are hydrogen.

Additionally preferred are cyclohexane derivatives of the formulae 1a, 1b and 1c where R1 and/or R2 are selected from C1- to C4-alkyl, especially C2- to C4-alkyl, more particularly from methyl, ethyl, n-propyl, isopropyl and tert-butyl.

Particularly preferred are cyclohexane derivatives of the formulae 1a, 1b and 1c where R1 is the same as R2, and R1 and R2 are selected from C1- to C4-alkyl, especially C2- to C4-alkyl, and more particularly selected from ethyl, n-propyl, isopropyl and tert-butyl.

Very particularly preferred are cyclohexane derivatives of the formulae 1a, 1b and 1c where R1 and R2 are ethyl.

Preferred cyclohexane derivatives are more particularly those of the formula 1a. Preferred among these are those in which the total number of carbon atoms in radicals R1 to R6 has a numerical value of not more than 15, more preferably of not more than 12, very preferably of not more than 8 and in particular of not more than 6. Particularly preferred are cyclohexane derivatives of the formula 1a which have a trans/cis ratio of at least 60:40, preferably of at least 70:30, more particularly of at least 80:20, more preferably of at least 90:10 and very preferably of at least 95:5, such as, for example, 98:2, 99:1 or 99.9:0.1 or higher. Further preferred are cyclohexane derivatives of the formula 1a where R1 is the same as R2. Further preferred are also cyclohexane derivatives of the formula 1a in which R3, R4, R5 and R6 are selected from hydrogen and methyl, and more particularly those in which R3, R4, R5 and R6 are hydrogen. Further preferred are cyclohexane derivatives of the formula 1a in which R1 and/or R2 are selected from C1- to C4-alkyl, more particularly from C2- to C4-alkyl, especially from methyl, ethyl, n-propyl, isopropyl and tert-butyl. Particularly preferred are cyclohexane derivatives of the formula 1a where R1 is the same as R2, and R1 and R2 are selected from C1- to C4-alkyl, more particularly from C2- to C4-alkyl, and especially from methyl, ethyl, n-propyl, isopropyl and tert-butyl. Very particularly preferred are cyclohexane derivatives of the formula 1a where R1 and R2 are ethyl.

Particularly preferred cyclohexane derivatives are those of the formula 1a in which R3, R4, R5 and R6 are selected from hydrogen and methyl, and more particularly those in which R3, R4, R5 and R6 are hydrogen, and in which R1 and R2 are selected from C1- to C4-alkyl, more particularly from C2- to C4-alkyl, more preferably from methyl, ethyl, n-propyl, isopropyl and tert-butyl, and especially preferably those in which R1 is the same as R2, and particularly in which R1 and R2 are ethyl. Among these particularly preferred cyclohexane derivatives of the formula 1a in which R3, R4, R5 and R6 are selected from hydrogen and methyl and are more particularly hydrogen, particular preference is given to those having a high cis/trans ratio of at least 70:30, more particularly of at least 80:20, more preferably of at least 90:10 and very preferably of at least 95:5, such as, for example, 98:2, 99:1 or 99.9:0.1 or higher. Among these particularly preferred cyclohexane derivatives of the formula 1a in which R3, R4, R5 and R6 are selected from hydrogen and methyl and are more particularly hydrogen, particular preference is likewise given to those having a high trans/cis ratio of at least 70:30, more particularly of at least 80:20, more preferably of at least 90:10 and very preferably of at least 95:5, such as, for example, 98:2, 99:1 or 99.9:0.1 or higher.

These preferred embodiments may be combined arbitrarily with one another.

Particularly preferred, accordingly, are cyclohexane derivatives having a total number of carbon atoms in radicals R1 to R6 of not more than 15 or less and a high fraction of the cis isomer of 70:30 or even higher.

Examples of preferred compounds of the formula 1a are 1,4-bis(ethoxymethyl)cyclohexane, 1,4-bis(n-propoxymethyl)cyclohexane, 1,4-bis(isopropoxymethyl)cyclohexane and 1,4-bis(tert-butoxymethyl)cyclohexane.

Particularly preferred, accordingly, are also bis(ethoxymethyl)cyclohexane derivatives (cyclohexane derivatives of the formulae 1a, 1b or 1c in which R1 and R2 are ethyl) having a high fraction of the cis isomer of 70:30 or higher.

Especially preferred is a bis(ethoxymethyl)cyclohexane derivative having a high fraction of the cis isomer of 70:30 or higher and a total number of carbon atoms in the radicals R1 to R6 of not more than 15 or less.

Particular preference is given to the 1,4-bis(ethoxymethyl)cyclohexane (cyclohexane derivative of the formula 1a with R1=R2=ethyl and R3=R4=R5=R6=hydrogen) which is enriched in terms of the cis isomer, more particularly 1,4-bis(ethoxymethyl)cyclohexane having a cis/trans ratio of at least 70:30, more preferably of at least 80:20 and very preferably of 99:1 or higher as disclosed above.

More particularly preferred is also the 1,4-bis(ethoxymethyl)cyclohexane which is enriched in terms of the trans isomer, having a trans/cis ratio of preferably at least 70:30, more preferably of at least 80:20 and very preferably of 99:1 or higher as disclosed above.

Also found has been the use of a cyclohexane derivative with a structure according to formula 1a, 1b or 1c (formula 1a, 1b, 1c)

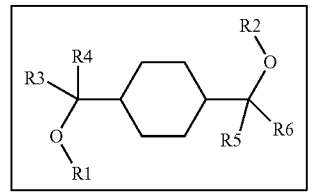

1a

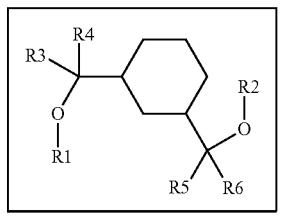

1b

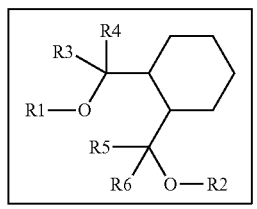

1c where the substituents on the cyclohexyl ring may be in cis or trans position to one another, and
  a) for formula 1a
    R1 is selected from the group of Ra and hydrogen, and
    R2 is selected from the group Ra, and
    the radicals R3 to R6 independently of one another are selected from the group of Ra and hydrogen, and
    where the following provisos apply:
    R1 is not hydrogen if all radicals R3 to R6 are hydrogen, and
    R2 is not C1- to C3-alkyl if R1 is hydrogen and at least one radical from R3 to R6 is selected from C1- to C3-alkyl, and
    at least one radical from R3 to R6 is not hydrogen if R1 is hydrogen and R2 is selected from the group Ra,
  b) for formula 1b and formula 1c
    R1 to R6 independently of one another are selected from the group of Ra and hydrogen, and at least one radical from R1 and R2 is not hydrogen,
    where the group Ra consists of C1- to C6-alkyl, C3- to C6-cycloalkyl, C3- to C6-cycloalkenyl and C2- to C6-alkenyl,
  with the proviso that the summed total number of carbon atoms in all radicals R1 to R6 for formulae 1a, 1b and 1c is in each case only a whole numerical value from 2 to 20,
as aroma compound, i.e. as fragrance and/or flavoring, or as formulation auxiliary.

The inventive use encompasses more particularly use in preparations which typically comprise at least one aroma compound, i.e. at least one fragrance and/or flavoring. Such preparations include laundry and cleaning detergents, cosmetic preparations, perfumes, other fragranced hygiene articles (diapers, sanitary towels, armpit pads, paper towels, wet wipes, toilet paper, pocket tissues, etc.), foods, food supplements, examples being chewing gums or vitamin products, fragrance dispensers, examples being room air fresheners, and pharmaceutical preparations, and also crop protection products.

The inventive use encompasses not only the formulating of a preparation which typically comprises at least one aroma compound with at least one cyclohexane derivative of the formulae 1a, 1b and/or 1c and optionally with one or more other aroma compounds, e.g. the incorporation of at least one cyclohexane derivative of the formulae 1a, 1b and/or 1c, optionally together with one or more other aroma compounds, into an existing preparation which before comprises no aroma compound. Typically comprises at least one fragrance and/or flavoring and also the production of a preparation which typically comprises at least one aroma compound using at least one cyclohexane derivative of the formulae 1a, 1b and/or 1c, optionally together with one or more other aroma compounds, e.g. by mixing or treating the other constituents of the preparation with at least one cyclohexane derivative of the formulae 1a, 1b and/or 1c and optionally with one or more other aroma compounds.

The cyclohexane derivatives of the formulae 1a, 1b and 1c preferably find use for the production of laundry detergents and cleaning detergents, for the production of other fragranced hygiene articles, or use in laundry detergents and cleaning detergents and in other fragranced hygiene articles, and also use for producing cosmetic preparations and use in cosmetic preparations. Cyclohexane derivatives of the formulae 1a, 1b and 1c find use, furthermore, in foods, in food supplements, examples being chewing gums or vitamin preparations, in fragrance dispensers, for example room air fresheners, in pharmaceutical preparations, in crop protection products or for producing foods, food supplements, fragrance dispensers, pharmaceutical preparations, or crop protection products.

Particular preference is given to use in cosmetic preparations. More particular preference is given to use in fragrance-comprising preparations such as perfumes. Also particularly preferred is the use of the cyclohexane derivatives of the formulae 1a, 1b and/or 1c in laundry and cleaning detergents and for producing laundry and cleaning detergents.

The definition of the radicals R1 to R6 is as defined above.
Preferred cyclohexane derivatives of the formulae 1a, 1b and 1c used have as a total number of carbon atoms in radicals R1 to R6 a numerical value of not more than 15, more preferably of not more than 12, very preferably of not more than 8 and more particularly of not more than 6. Also used with preference are cyclohexane derivatives of the formulae 1a, 1b and 1c in which R1 and R2 are not hydrogen (diethers).

Additionally preferred for use are cyclohexane derivatives of the formulae 1a, 1b and 1c which are enriched in terms of the cis isomer or the trans isomer. Preference is given more particularly to cyclohexane derivatives of the formulae 1a, 1b and 1c which are enriched in terms of the cis isomer or the trans isomer and whose cis/trans ratio, i.e. the ratio by mass or by moles of cis isomer to trans isomer, has a value of 60:40 and more particularly at least 70:30. Likewise preferred are cyclohexane derivatives of the formulae 1a, 1b and 1c in which the trans/cis ratio, i.e. the ratio by mass or by moles of trans isomer to cis isomer, has a value of at least 60:40 and more particularly at least 70:30. Particularly preferred are cyclohexane derivatives of the formulae 1a, 1b and 1c having a cis/trans ratio or those having a trans/cis ratio of at least 80:20, very preferably of at least 90:10 and more particularly of at least 95:5, such as, for example, 98:2, 99:1 or 99.9:0.1 or higher.

Especially preferred are cyclohexane derivatives of the formulae 1a, 1b and 1c having a cis/trans ratio or those having a trans/cis ratio of at least 99:1.

Further preferred for use are cyclohexane derivatives of the formulae 1a, 1b and 1c where R1 is the same as R2.

Further preferred for use are also cyclohexane derivatives of the formulae 1a, 1b and 1c where R1 to R4 are methyl, and more particularly those in which R5 and R6 are hydrogen.

Further preferred for use are also cyclohexane derivatives of the formulae 1a, 1b and 1c in which R3, R4, R5 and R6 are selected from hydrogen and methyl, and more particularly those in which R3, R4, R5 and R6 are hydrogen.

Additionally preferred are cyclohexane derivatives of the formulae 1a, 1b and 1c where R1 and/or R2 are selected from C1- to C4-alkyl, especially C2- to C4-alkyl, more particularly from methyl, ethyl, n-propyl, isopropyl and tert-butyl.

Particularly preferred for use are cyclohexane derivatives of the formulae 1a, 1b and 1c where R1 is the same as R2, and R1 and R2 are selected from C1- to C4-alkyl, especially C2- to C4-alkyl, and more particularly selected from ethyl, n-propyl, isopropyl and tert-butyl.

Very particularly preferred for use are cyclohexane derivatives of the formulae 1a, 1b and 1c where R1 and R2 are ethyl.

In relation to the inventive use, cyclohexane derivatives of the formula 1a are preferred. Preferred among these are those in which the total number of carbon atoms in radicals R1 to R6 has a numerical value of not more than 15, more preferably of not more than 12, very preferably of not more than 8 and in particular of not more than 6. Particularly preferred for use are cyclohexane derivatives of the formula 1a which have a trans/cis ratio of at least 60:40, preferably of at least 70:30, more particularly of at least 80:20, more preferably of at least 90:10 and very preferably of at least 95:5, such as, for example, 98:2, 99:1 or 99.9:0.1 or higher. Further preferred for use are cyclohexane derivatives of the formula 1a where R1 is the same as R2. Further preferred for use are also cyclohexane derivatives of the formula 1a in which R3, R4, R5 and R6 are selected from hydrogen and methyl, and more particularly those in which R3, R4, R5 and R6 are hydrogen. Further preferred for use are cyclohexane derivatives of the formula 1a in which R1 and/or R2 are selected from C1- to C4-alkyl, more particularly from C2- to C4-alkyl, especially from methyl, ethyl, n-propyl, isopropyl and tert-butyl. Particularly preferred for use are cyclohexane derivatives of the formula 1a where R1 is the same as R2, and R1 and R2 are selected from C1- to C4-alkyl, more particularly from C2- to C4-alkyl, and especially from methyl, ethyl, n-propyl, isopropyl and tert-butyl. Very particularly preferred for use are cyclohexane derivatives of the formula 1a where R1 and R2 are ethyl.

In relation to the use, particular preference is given to cyclohexane derivatives of the formula 1a in which R3, R4, R5 and R6 are selected from hydrogen and methyl, and more particularly those in which R3, R4, R5 and R6 are hydrogen, and in which R1 and R2 are selected from C1- to C4-alkyl, more particularly from C2- to C4-alkyl, more preferably from methyl, ethyl, n-propyl, isopropyl and tert-butyl, and especially preferably those in which R1 is the same as R2, and particularly in which R1 and R2 are ethyl. Among these particularly preferred cyclohexane derivatives of the formula 1a in which R3, R4, R5 and R6 are selected from hydrogen and methyl and are more particularly hydrogen, particular preference is given to those having a high cis/trans ratio of at least 70:30, more particularly of at least 80:20, more preferably of at least 90:10 and very preferably of at least 95:5, such as, for example, 98:2, 99:1 or 99.9:0.1 or higher. Among these particularly preferred cyclohexane derivatives of the formula 1a in which R3, R4, R5 and R6 are selected from hydrogen and methyl and are more particularly hydrogen, particular preference is likewise given to those having a high trans/cis ratio of at least 70:30, more particularly of at least 80:20, more preferably of at least 90:10 and very preferably of at least 95:5, such as, for example, 98:2, 99:1 or 99.9:0.1 or higher.

These preferred and also the particularly preferred embodiments can be combined arbitrarily with one another.

Particularly preferred, accordingly, are cyclohexane derivatives of the formulae 1a, 1b and 1c, more particularly those of the formula 1a, having a total number of carbon atoms in radicals R1 to R6 of not more than 15 or less and a high fraction of the cis isomer of 70:30 or higher as disclosed above. Particularly preferred, accordingly, are also bis(ethoxymethyl)cyclohexane derivatives of the formulae 1a, 1b and 1c, more particularly those of the formula 1a, having a high fraction of the cis isomer of 70:30 or higher as disclosed above.

Especially preferred are bis(ethoxymethyl)cyclohexane derivatives of the formulae 1a, 1b and 1c, more particularly those of the formula 1a, having a high fraction of the cis isomer of 70:30 or higher and a total number of carbon atoms in the radicals R1 to R6 of not more than 15 or less.

Particularly preferred is the 1,4-bis(ethoxymethyl)cyclohexane (cyclohexane derivative of the formula 1a with R1=R2=ethyl and R3=R4=R5=R6=hydrogen) which is enriched in terms of the cis isomer, more particularly 1,4-bis(ethoxymethyl)cyclohexane having a cis/trans ratio of at least 70:30, more particularly of at least 80:20, more preferably of at least 95:5 and very preferably of 99:1 or higher as disclosed above, as fragrance and/or as formulation auxiliary in preparations which comprise fragrances, such as, more particularly, in perfumes. It finds use with more particular preference as a fragrance in preparations which comprise fragrances.

Particularly preferred is the 1,4-bis(ethoxymethyl)cyclohexane (cyclohexane derivative of the formula 1a with R1=R2=ethyl and R3=R4=R5=R6=hydrogen) which is enriched in terms of the trans isomer, more particularly 1,4-bis(ethoxymethyl)cyclohexane having a trans/cis ratio of at least 70:30, more particularly of at least 80:20, more preferably of at least 95:5 and very preferably of 99:1 or higher as disclosed above, as fragrance and/or as formulation auxiliary in preparations which comprise fragrances, such as, more particularly, in perfumes. It finds use with more particular preference as a formulation auxiliary in preparations which comprise fragrances.

In relation to the inventive use, the compounds of the formula 1 that are identified below are particularly preferred examples: 1,4-bis(methoxymethyl)cyclohexane, 1,4-bis(ethoxy methyl)cyclohexane, 1,4-bis(vinyloxymethyl)cyclohexane, 1,4-bis(n-propoxymethyl)cyclohexane, 1,4-bis(isopropoxymethyl)cyclohexane and 1,4-bis(tert-butoxymethyl)cyclohexane.

Additionally found has been a process for preparing a cyclohexane derivative with a structure of the formula 1a, 1b or 1c (formula 1a, 1b, 1c)

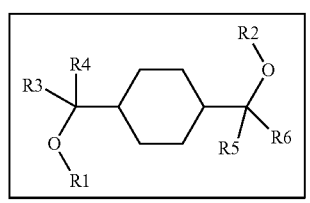

1a

-continued

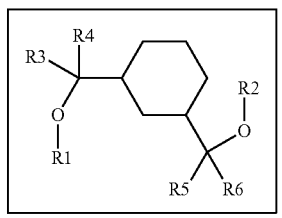

1b

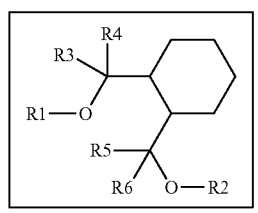

1c where the substituents on the cyclohexyl ring may be in cis or trans position to one another, and R1 and R2 independently of one another are selected from the group consisting of Rb and hydrogen, and R3 to R6 independently of one another are selected from the group consisting of Ra and hydrogen, where the group Ra consists of C1- to C6-alkyl, C3- to C6-cycloalkyl, C3- to C6-cycloalkenyl, C2- to C6-alkenyl and the group Rb consists of C1- to C6-alkyl, C3- to C6-cycloalkyl and C2- to C6-alkenyl, with the provisos that at least one radical from R1 and R2 is selected from C2- to C6-alkenyl, and that the summed total number of carbon atoms in all radicals R1 to R6 in the cyclohexane derivative of the formula 1 may only adopt a whole numerical value from 2 to 20, characterized in that a cyclohexane derivative of the corresponding formula 2a, 2b or 2c (formula 2a, 2b, 2c)

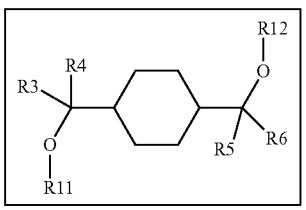

2a

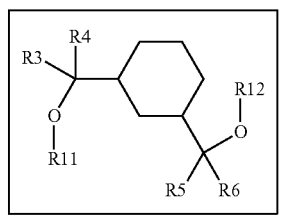

2b

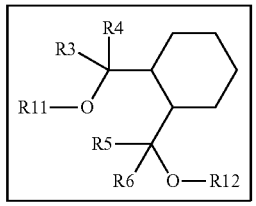

2c is reacted with at least one C2- to C6-alkyne, to give a cyclohexane derivative of the formula 1a, 1b or 1c, where, in the cyclohexane derivative of the formulae 2a, 2b and 2c, R3, R4, R5 and R6 independently of one another are selected from the group consisting of Ra and hydrogen, R11 and R12 are hydrogen or a group Rd, where at least one of the radicals, R11 and/or R12, is hydrogen, where Ra is a group consisting of C1- to C6-alkyl, C3- to C6-cycloalkyl, C3- to C6-cycloalkenyl and C2- to C6-alkenyl, and Rd is a group consisting of C1- to C6-alkyl, C3- to C6-cycloalkyl and C2- to C6-alkenyl, where the radicals R11, R12, R3, R4, R5 and R6 and the alkyne are selected such that the summed total number of carbon atoms in all radicals R1 to R6 in the resultant compounds of the formulae 1a, 1b and 1c, respectively, is a whole numerical value from 2 to 20, and where a cyclohexane derivative of the formulae 1a, 1b and/or 1c is obtained, in which R1 is selected from C2- to C6-alkenyl if R11 is hydrogen, and in which R2 is selected from C2- to C6-alkenyl if R12 is hydrogen.

The invention accordingly also provides a process for preparing a cyclohexane derivative with a structure according to formula 1a, 1b or 1c, comprising the reaction of a cyclohexane derivative of the corresponding formula 2a, 2b or 2c with at least one C2- to C6-alkyne, with the exception of a process for preparing a cyclohexane derivative of the formula 1a in which R1 and/or R2 are vinyl if R3, R4, R5 and R6 are hydrogen.

The definition of the radicals R1 to R6 and also of the radicals R11 and R12 is as defined above. It is self-evident that when reacting a cyclohexane derivative of the formulae 2a, 2b and/or 2c with a C2- to C6-alkyne, the radicals R3, R4, R5 and R6 remain unchanged, i.e. correspond to one another in the starting material of the formulae 2a, 2b and 2c and in the resultant cyclohexane derivative of the formulae 1a, 1b and 1c. Similarly, the cis/trans ratio in the resultant cyclohexane derivative of the formulae 1a, 1b and 1c will correspond to the cis/trans ratio in the starting material of the formulae 2a, 2b and 2c. The reaction of the cyclohexane derivative of the formula 2a yields a cyclohexane derivative of the formula 1a; the reaction of the cyclohexane derivative of the formula 2b yields a cyclohexane derivative of the formula 1 b; and the reaction of the cyclohexane derivative of the formula 2c yields a cyclohexane derivative of the formula 1c.

Preference is given to a process where, in the cyclohexane derivative of the formulae 2a, 2b and/or 2c, R11 and R12 are hydrogen and accordingly, in the resultant cyclohexane derivative of the formulae 1a, 1b and 1c, the radicals R1 and R2 are selected from C2- to C6-alkenyl.

Likewise preferred is a process in which, in the cyclohexane derivative of the formulae 1a, 1b and 1c obtained in accordance with the invention, R1 is the same as R2, i.e. both radicals, R1 and R2, stand for the same C2- to C6-alkenyl radical.

Likewise preferred is a process in which the $C_2$-$C_6$-alkyne reacted in the process is ethyne. In this case a cyclohexane derivative of the formulae 1a, 1b and 1c is obtained in which R1 and/or R2 are vinyl (=ethenyl).

Preferred cyclohexane derivatives of the formulae 1a, 1b and 1c that are prepared additionally have, as the total number of carbon atoms in the radicals R1 to R6, a numerical value of not more than 15, more preferably of not more than 12, very preferably of not more than 8 and more particularly of not more than 6. Accordingly, the cyclohexane derivative of the formulae 2a, 2b and 2c and the alkyne are selected such that the total carbon number of alkyne and the radicals R11, R12, R3, R4, R5 and R6 in the cyclohexane derivative of the formulae 2a, 2b and 2c has a numerical value of not more than 15, more preferably of not more than 12, very preferably of not more than 8 and more particularly of not more than 6.

With further preference, cyclohexane derivatives of the formulae 2a, 2b and 2c are used whose cis/trans ratio or whose trans/cis ratio in each case has a value of at least 70:30. Particularly preferred are those having a ratio of at least 80:20, very preferably of at least 90:10 and more particularly of at least 95:5, such as, for example, 98:2, 99:1 or 99.9:0.1 or higher. Especially preferred are values of at least 99:1.

The process described above is suitable preferably for preparing cyclohexane derivatives of the formulae 1a, 1b and 1c in which R1 and R2 have the same definition and accordingly stand for the same C2- to C6-alkeny radical.

The above-described process is suitable preferably for preparing cyclohexane derivatives of the formulae 1a, 1b and 1c in which R1 and/or R2 and more particularly both R1 and R2 stand for a C2- to C6-alkenyl radical of the formula $CH_2=C(\#)$—$R^x$, in which # stands for the link to the oxygen atom in the cyclohexane derivatives of the formulae 1a, 1b and 1c, and Rx is hydrogen or C1- to C4-alkyl, more particularly hydrogen, methyl or ethyl, and especially hydrogen.

The above-described process is suitable preferably for preparing cyclohexane derivatives of the formulae 1b and 1c in which R1 and R2 are selected from vinyl and isopropenyl (=2-propenyl).

The above-described process is suitable more particularly for preparing cyclohexane derivatives of the formulae 1a, 1b and 1c in which R3, R4, R5 and R6 are selected from methyl and hydrogen and more particularly are hydrogen.

The above-described process is suitable with particular preference for preparing cyclohexane derivatives of the formulae 1b and 1c in which R1 and R2 are vinyl and R3, R4, R5 and R6 are hydrogen.

The above-described process is also suitable for preparing cyclohexane derivatives of the formula 1a in which R1 and R2 are isopropenyl and R3 to R6 are hydrogen.

The above-described process is additionally suitable for preparing cyclohexane derivatives of the formula 1a in which R1 and R2 are vinyl and R3 to R6 are hydrogen.

These preferred and also the particularly preferred embodiments can be combined arbitrarily with one another.

Particularly preferred, accordingly, is the preparation of cyclohexane derivatives of the formulae 1a, 1b and 1c having a total number of carbon atoms in the radicals R1 to R6 of not more than 15 or less and a high fraction of the cis isomer of 70:30 or higher as disclosed above.

Particularly preferred accordingly is also the preparation of a bis(vinyloxymethyl)cyclohexane derivative of the formulae 1a, 1b and 1c having a high fraction of the cis isomer of 70:30 or higher as disclosed above.

Especially preferred is the preparation of a bis(vinyloxymethyl)cyclohexane derivative of the formulae 1a, 1b and 1c having a high fraction of the cis isomer of 70:30 or higher as disclosed above and a total number of carbon atoms in the radicals R1 to R6 of not more than 15 or less.

More particularly preferred for formulae 1b and 1c is the preparation of bis(vinyloxymethyl)cyclohexane.

More particularly preferred for the formulae 1b and 1c is the preparation of bis(vinyloxymethyl)cyclohexane having a high cis/trans ratio of preferably at least 70:30, more particularly of at least 80:20 and very preferably of at least 95:5, and especially of at least 99:1.

More particularly preferred for the formula 1a is the preparation of bis(isopropenyloxymethyl)cyclohexane.

More particularly preferred for the formula 1a is the preparation of bis(vinyloxymethyl)cyclohexane.

More particularly preferred for the formula 1a is the preparation of bis(isopropenyloxymethyl)cyclohexane having a high cis/trans ratio of preferably at least 70:30, more particularly of at least 80:20 and more preferably of at least 95:5, and especially of at least 99:1.

The reaction of the cyclohexane derivative of the formulae 2a, 2b and/or 2c with the C2- to C6-alkyne may be known in analogy to methods known in principle for the alkenylation of alkanols with alkynes, as for example from the above-cited specifications WO 90/09364, U.S. Pat. No. 5,183,946 and U.S. Pat. No. 4,751,273, and also from the scientific literature (see, for example, J. March "Advanced Organic Chemistry" $3^{rd}$ edition Wiley Interscience 1985, p. 684 and literature reference 148 cited therein). The necessary reaction conditions can be determined by the skilled person by means of routine methods, starting, for example, from the conditions specified in the literature and in the examples of the present application.

Generally speaking, the reaction of the cyclohexane derivative of the formulae 2a, 2b and/or 2c with the C2- to C6-alkyne takes place in the presence of at least one base, preferably at least one oxo base, which is frequently selected from alkali metal hydroxides, alkaline earth metal hydroxides, alkali metal carbonates, alkaline earth metal carbonates, alkali metal alkoxides, more particularly alkali metal (C1- to C4-alkanolates), alkaline earth metal alkoxides, more particularly alkaline earth metal (C1- to C4-alkanolates) and mixtures thereof, for example from the hydroxides, carbonates and C1- to C4-alkanolates of lithium, sodium, potassium, cesium, magnesium or calcium. Preferred oxo bases are those selected from the hydroxides and C1- to C4-alkanolates of alkali metals and alkaline earth metal hydroxides. The oxo bases are selected more particularly from alkali metal hydroxides and alkaline earth metal hydroxides, especially from calcium, potassium and sodium hydroxides. Particularly preferred is potassium hydroxide. Likewise particularly preferred are the sodium and potassium (C1- to C4-alkanolates) such as sodium methylate, potassium methylate, sodium ethylate, potassium ethylate, sodium isopropanolate, potassium isopropanolate, sodium n-butanolate, potassium n-butanolate, sodium isobutanolate, potassium isobutanolate and sodium tert-butanolate, potassium tert-butanolate, and of these preferably potassium methylate, potassium ethylate and potassium isobutanolate. Instead of the oxo base it is also possible to use basic transition metal compounds, preferably the salts of carboxylic acids, more particularly the zinc salts and the cadmium salts of carboxylic acids such as zinc acetate and zinc naphthenate. The base may be used stoichiometrically or catalytically in relation to the cyclohexane derivative of the formulae 2a, 2b and/or 2c. It is preferred to use the base in catalytic amounts, more particularly in an amount of 0.01 to 0.5 mol, especially in an amount of 0.02 to 0.2 mol, per mole of the cyclohexane derivative of the formulae 2a, 2b and/or 2c.

The reaction of cyclohexane derivative of the formulae 2a, 2b and/or 2c with the C2- to C6-alkyne may be carried out in bulk or in a diluent. Preferred diluents are organic solvents which have no reactive NH or OH group, examples being cyclic ethers such as tetrahydrofuran, methyltetrahydrofuran and dioxane, and dialkyl ethers, examples being methyl tert-butyl ether, ethyl tert-butyl ether, diethyl ether and diisopropyl ether. Suitable diluents are also secondary alkanols, such as isopropanol and 2-butanol, especially if the cyclohexane derivative of the formulae 2a, 2b and/or 2c has only primary OH groups (R3, R4=H if R11=H, or R5, R6=H if R12=H). Clearly, mixtures of the aforementioned diluents can also be used. In one preferred embodiment of the process, the reaction of the cyclohexane derivative of the formulae 2a, 2b and/or 2c with the C2- to C6-alkyne takes place in bulk.

It is preferred to use a C2- to C6-alkyne of the formula HC≡C—R$^x$, in which R$^x$ is C1- to C4-alkyl or hydrogen and more particularly hydrogen, methyl or ethyl. More particularly the alkyne is ethyne (R$^x$=H).

The reaction of cyclohexane derivative of the formulae 2a, 2b and/or 2c with the C2- to C6-alkyne takes place in general at elevated temperature, preferably at temperatures in the range from 100 to 300° C., more particularly at temperatures in the range from 120 to 200° C., and especially in the range from 140 to 160° C. The reaction pressure is of course dependent on the volatility of the reactants used and of the product, and also on the reaction temperature. The reaction of cyclohexane derivative of the formulae 2a, 2b and/or 2c with the C2- to C6-alkyne takes place preferably under autogenous pressure, which is situated typically in the range from 2 bar to 40 bar, more particularly in the range from 5 to 30 bar, more preferably in the range from 10 to 20 bar and especially in the range from 16 to 20 bar. For safety reasons, in industrial units, the pressure is generally limited: in the case of ethyne it is limited, for example, usually to about 20 bar, and to somewhat higher pressures in the case of higher (less volatile) alkynes.

For the reaction of the cyclohexane derivative of the formulae 2a, 2b and/or 2c with the C2- to C6-alkyne, the reactants may be charged to a suitable reaction vessel and brought to reaction conditions. It has proven advantageous to introduce the cyclohexane derivative of the formulae 2a, 2b and/or 2c, optionally together with the base, into the reaction vessel and to add at least a portion of the alkyne, preferably at least 80% of the alkyne and more particularly the total amount of the alkyne, in the course of the reaction.

The alkynylation, for instance the preparation of cyclohexanedimethanol monovinyl and divinyl ethers, may be carried out as follows:
an autoclave rendered inert using inert gas, e.g. nitrogen or argon, is charged with cyclohexanedimethanol together with alkali metal hydroxide such as potassium hydroxide—optionally, also, additionally a solvent such as isopropanol—, and this initial charge is melted and heated to temperatures of more than 140° C., for instance 160° C. The alkyne, for example ethyne, is added: in the case of gaseous alkyne such as ethyne, it is injected as a gas to total pressures of about 10 to 20 bar, and the amount of alkyne needed to maintain the pressure is supplemented continuously. After a reaction time of about 5 to 15 hours or alternatively—in the case of gaseous alkyne—after a defined gas uptake (calculated by the stoichiometry of the reaction and the amount of cyclohexanedimethanol or derivative thereof, taking account of a suitable excess—generally a large excess—of alkyne), the reaction is ended and also, optionally, the supply of gaseous alkyne is ended, and the reaction mixture is cooled to room temperature, let down and—in the case of gaseous alkyne—flushed with nitrogen. Depending on the purity of the resultant products or product mixtures, which can be determined, for instance, by chromatography, it is possible for a purification to take place if products of higher purity are required. A possible purification is by distillation using known columns and column packings.

The radicals R3 to R6 in formulae 2a, 2b and 2c correspond in this process to the radicals R3 to R6 in the formulae 1a, 1b and 1c, respectively, unless any reaction takes place at one of these positions: R6 in formula 2a, 2b or 2c corresponds, for example, to R6 in formula 1a, 1b or 1c, respectively, if no reaction with the alkyne takes place at the position of R6 in formula 2a, 2b or 2c.

Whether a reaction takes place at one of the positions or not is something which the skilled person can easily determine on the basis of his or her art knowledge with customary methods such as analysis and also, optionally, by theoretical considerations on the basis of the art knowledge. Generally speaking, there is no reaction with the alkyne at the radicals R3 to R6 in formulae 2a, 2b and 2c.

Additionally found has been a process for preparing a cyclohexane derivative with a structure according to formula 1a, 1b or c (formula 1a, 1b, 1c)

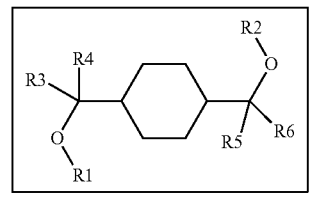

1a

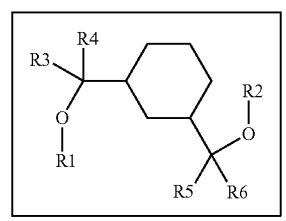

1b

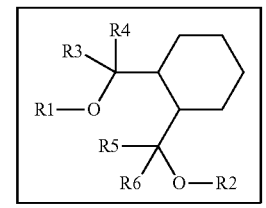

1c where the substituents on the cyclohexyl ring may be in cis or trans position to one another, and R1 is selected from the group consisting of Rc and hydrogen, and R2 is selected from the group consisting of Rc, and the radicals R3 to R6 independently of one another are selected from the group consisting of Rc and hydrogen, where Rc is a group consisting of C1- to C6-alkyl and C3- to C6-cycloalkyl, with the proviso that the summed total number of carbon atoms in all radicals R1 to R6 in the cyclohexane derivative of the formula 1 may only adopt a whole numerical value of 2 to 20, and with the further proviso that at least one of the radicals R1 to R6 is C2- to C6-alkyl or C3- to C6-cycloalkyl;

which comprises obtaining the cyclohexane derivative of the formula 1a, 1b or 1c by hydrogenation of a cyclohexane derivative of the respective formula 3a, 3b or 3c with hydrogen, (formula 3a, 3b, 3c)

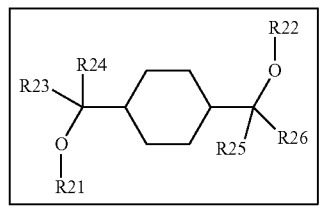

3a

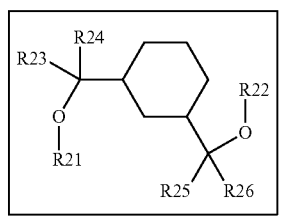

3b

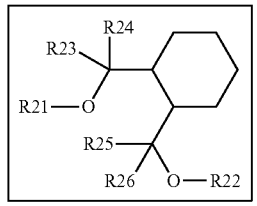

3c where, in the cyclohexane derivative of the formulae 3a, 3b and 3c

R21 is selected from the group consisting of Re and hydrogen, and

R22 is selected from the group consisting of Re, and the radicals R23 to R26 independently of one another are selected from the group consisting of Re and hydrogen, and where Re is a group consisting of C1- to C6-alkyl, C3- to C6-cycloalkyl, C3- to C6-cycloalkenyl and C2- to C6-alkenyl, where at least one of the radicals R21 to R26 is selected from the group consisting of C3- to C6-cycloalkenyl and C2- to C6-alkenyl, and where the radicals R21 to R26 are selected such that the summed total number of carbon atoms in all radicals R1 to R6 may only represent a whole numerical value from 2 to 20.

The invention accordingly also provides a process for preparing a cyclohexane derivative with a structure according to formula 1a, 1b or 1c, comprising the hydrogenation of a cyclohexane derivative of the corresponding formula 3a, 3b or 3c with hydrogen.

The definition of the radicals R1 to R6 and also the radicals R21 to R26 is as defined above.

The radicals R21 to R26 in the formulae 3a, 3b and 3c correspond in the case of this process to the radicals R1 to R6, provided no reaction takes place at one of these positions: R26 corresponds, for example, to R6 if no reaction with the hydrogen takes place at the position of R26, which is generally the case if R26 is hydrogen, C1- to C6-alkyl or C3- to C6-cycloalkyl. Accordingly, R25 corresponds to R5, R24 to the radical R4, R23 to the radical R3, R22 to the radical R2, R21 to the radical R1, if no reaction with the hydrogen takes place at the position of R21, R22, R23, R24 or R25, respectively, which is generally the case if these radicals are hydrogen, C1- to C6-alkyl or C3- to C6-cycloalkyl.

Whether a reaction takes place at one of the positions or not is something the skilled person can easily determine on the basis of his or her art knowledge with customary methods such as analysis and also, optionally, by theoretical considerations on the basis of the art knowledge.

Similarly, the cis/trans ratio in the resultant cyclohexane derivative of the formulae 1a, 1b and 1c will correspond to the cis/trans ratio in the starting material of the formulae 3a, 3b and 3c. The reaction of the cyclohexane derivative of the formula 3a yields a cyclohexane derivative of the formula 1a, the reaction of the cyclohexane derivative of the formula 3b yields a cyclohexane derivative of the formula 1 b, and the reaction of the cyclohexane derivative of the formula 3c yields a cyclohexane derivative of the formula 1c. The number of carbon atoms in a radical R1, R2, R3, R4, R5 and R6 in the formulae 1a, 1b and/or 1c corresponds of course to the number of carbon atoms in the corresponding radical R21, R22, R23, R24, R25 and R26 in the formulae 3a, 3b and/or 3c.

Preference is given to a process in which, in the cyclohexane derivative of the formulae 3a, 3b and/or 3c, R1 is hydrogen and R2 is selected from C2- to C6-alkenyl, affording a compound of the formulae 1a, 1b and/or 1c in which R1 is hydrogen and R2 is selected from C2- to C6-alkyl.

Further preferred is a process in which, in the cyclohexane derivative of the formula 3, R1 and R2 independently of one another are selected from C2- to C6-alkenyl, affording a compound of the formulae 1a, 1b and/or 1c in which R1 and R2 are selected from C2- to C6-alkyl.

Further preferred is a process in which, in the cyclohexane derivative of the formula 3, R1 and R2 are selected from C2- to C6-alkenyl and R1 is the same as R2.

Further preferred is a process in which the alkenyl group is a C2-alkenyl (=vinyl or ethenyl).

Further preferred is a process in which the alkenyl group is a C3-alkenyl, namely 3-propenyl (=allyl) or 2-propenyl (isopropenyl).

The process described above is especially suitable for hydrogenating cyclohexane derivatives of the formulae 3a, 3b and 3c in which R23, R24, R25 and R26 are selected from methyl and hydrogen and more particularly are hydrogen, affording corresponding cyclohexane derivatives of the formulae 1a, 1b and/or 1c in which R3, R4, R5 and R6 are selected from methyl and hydrogen and more particularly are hydrogen.

The above-described process is suitable with particular preference for hydrogenating cyclohexane derivatives of the formulae 3a, 3b and 3c in which R21 and R22 are vinyl and R23, R24, R25 and R26 are hydrogen, affording corresponding cyclohexane derivatives of the formulae 1a, 1b and/or 1c in which R3, R4, R5 and R6 are hydrogen and R1 and R2 are ethyl.

The above-described process is suitable with particular preference for hydrogenating cyclohexane derivatives of the formulae 3a, 3b and 3c in which R1 and R2 are isopropenyl and R23, R24, R25 and R26 are hydrogen, affording corresponding cyclohexane derivatives of the formulae 1a, 1b and/or 1c in which R3, R4, R5 and R6 are hydrogen and R1 and R2 are 2-propyl (=isopropyl).

The above-described process is also suitable with particular preference for hydrogenating cyclohexane derivatives of the formulae 3a, 3b and 3c in which R1 and R2 are 3-propenyl (=allyl) and R23, R24, R25 and R26 are hydrogen, affording corresponding cyclohexane derivatives of the formulae 1a, 1b and/or 1c in which R3, R4, R5 and R6 are hydrogen and R1 and R2 are n-propyl.

Preferred cyclohexane derivatives of the formulae 1a, 1b and 1c that are prepared additionally have, as the total number of carbon atoms in radicals R1 to R6, a numerical value of not more than 15, more preferably of not more than 12, very preferably of not more than 8 and more particularly of not more than 6.

Furthermore, cyclohexane derivatives of the formulae 3a, 3b and/or 3c that are subjected to hydrogenation are preferably those having a high cis/trans ratio or a high trans/cis ratio, preferably those cyclohexane derivatives of the formulae 3a, 3b and/or 3c whose cis/trans ratio or whose trans/cis ratio in each case has a value of at least 70:30. Particularly preferred are those having a ratio of at least 80:20, very preferably of at least 90:10 and more particularly of at least 95:5, such as, for example, 98:2, 99:1 or 99.9:0.1 or higher. Especially preferred are values of at least 99:1.

Additionally, cyclohexane derivatives of the formulae 3a, 3b and/or 3b that are subjected to hydrogenation are preferably those in which R1 is the same as R2, i.e. in which R1 and R2 are the same C2- to C6-alkenyl radical.

Furthermore, cyclohexane derivatives of the formulae 1a, 1b and 1c that are obtainable by the hydrogenation in accordance with the invention are preferably those in which R1 and/or R2 are selected from ethyl, n-propyl, isopropyl and tert-butyl.

These preferred and particularly preferred embodiments may be combined arbitrarily with one another.

Particularly preferred, accordingly, is the preparation of cyclohexane derivatives of the formulae 1a, 1b and 1c having a total number of carbon atoms in radicals R1 to R6 of not more than 15 or less and a high fraction of the cis isomer of preferably at least 70:30, more particularly at least 80:20 and more preferably of at least 95:5, and especially at least 99:1, by hydrogenation of a corresponding cyclohexane derivative of the formulae 3a, 3b and/or 3c having a total number of carbon atoms in radicals R21 to R26 of not more than 15 or less and a high fraction of the cis isomer of preferably at least 70:30, more particularly at least 80:20 and very preferably of at least 95:5, and especially at least 99:1.

Particularly preferred, accordingly, is also the preparation of a bis(ethoxymethyl)cyclohexane derivative having a high fraction of the cis isomer of preferably at least 70:30, more particularly at least 80:20 and more preferably of at least 95:5, and especially at least 99:1, by hydrogenation of a corresponding bis(vinyloxymethyl)cyclohexane derivative which has the high fraction of the cis isomer of preferably at least 70:30, more particularly at least 80:20 and more preferably of at least 95:5, and especially at least 99:1.

With particular preference, cyclohexane derivatives of the formulae 1a, 1b and/or 1c in which R1 and/or R2 are selected from ethyl, n-propyl and isopropyl, very preferably only from ethyl, are prepared by hydrogenating a corresponding cyclohexane derivative of the formulae 3a, 3b and/or 3c in which R21 and/or R22 are vinyl, allyl or isopropenyl.

With particular preference, cyclohexane derivatives of the formulae 1a, 1b and/or 1c in which R1 and/or R2 are selected from ethyl, n-propyl and isopropyl and especially are ethyl and R3, R4, R5 and R6 are hydrogen are prepared by hydrogenating a corresponding cyclohexane derivative of the formulae 3a, 3b and/or 3c in which R21 and/or R22 are vinyl, allyl or isopropenyl and more particularly vinyl, and R23, R24, R25 and R26 are hydrogen.

Very particular preference is given to the preparation of a bis(ethoxymethyl)cyclohexane derivative having a high fraction of the cis isomer of preferably at least 70:30, more particularly at least 80:20 and very preferably of at least 95:5, and especially at least 99:1, and a total number of carbon atoms in the radicals R1 to R6 of not more than 15 or less, by hydrogenation of a corresponding bis(vinyloxymethyl)cyclohexane derivative which has a high fraction of the cis isomer of preferably at least 70:30, more particularly at least 80:20 and very preferably at least 95:5, and especially at least 99:1, and which has a total number of carbon atoms in radicals R1 to R6 of not more than 15 or less.

More particular preference is given to the preparation of 1,4-bis(ethoxymethyl)cyclohexane having a cis/trans ratio of preferably at least 70:30, more particularly at least 80:20 and more preferably of at least 95:5, and especially at least 99:1, by hydrogenation of the corresponding 1,4-bis(vinyloxymethyl)cyclohexane having a cis/trans ratio of preferably at least 70:30, more particularly at least 80:20 and more preferably of at least 95:5, and especially at least 99:1.

More particular preference is likewise given to the preparation of 1,4-bis(ethoxymethyl)cyclohexane having a trans/cis ratio of preferably at least 70:30, more particularly at least 80:20 and more preferably of at least 95:5, and especially at least 99:1, by hydrogenation of the corresponding 1,4-bis(vinyloxymethyl)cyclohexane having a trans/cis ratio of preferably at least 70:30, more particularly at least 80:20 and more preferably of at least 95:5, and especially at least 99:1.

The preparation of the compounds of the formula 1a, 1b or 1c by hydrogenation of the cyclohexane derivatives of the formula 3a, 3b or 3c, respectively, can be carried out in analogy to known processes for hydrogenating cycloalkane compounds which have olefinically unsaturated substituents.

In the process of the invention for the reduction of alkenyl groups in the cylohexane derivatives of the formulae 3a, 3b and/or 3c with hydrogen—both with and without immediately preceding alkynylation reaction—the reduction with hydrogen is carried out using gaseous hydrogen or hydrogen-containing gas mixtures. Besides hydrogen, such gas mixtures may comprise gases such as nitrogen or hydrocarbon-containing reformer offgases, but not catalyst poisons such as carbon monoxide, hydrogen sulfide or other sulfur-containing gases. It is preferred to use pure hydrogen (purity at least 99.9% by volume, preferably at least 99.95% by volume, more preferably at least 99.99% by volume).

Hydrogen here can be used in molecular or elemental form ("nascent hydrogen"). This nascent hydrogen can be obtained outside or within the reaction vessel, for example by reaction of molecular hydrogen with suitable precious metals, by electrolysis or by generation in situ with non-precious metals and water or suitable hydroxyl-containing compounds. It is preferred to use molecular hydrogen.

The reduction of cyclohexane derivatives of the formulae 3a, 3b and/or 3c with hydrogen is preferably performed using precious metals as catalysts.

Particularly preferred is the use of those precious metals which can be separated off by simple process operations, such as filtering, sieving or centrifuging. To this end, the precious metals are fixed for example in a fixed bed, such as solid particles, or in a column.

Precious metals for generating hydrogen are all substances known as such to the skilled person that are able, on contact with molecular hydrogen, to convert it into elemental hydrogen. Examples of such metals include platinum, palladium and nickel, in each case as the pure substance, as an alloy with one another or with other metals, and also mixtures comprising these metals or alloys, such as Raney nickel or palladium on oxidic support materials.

Non-precious metals for generating hydrogen are all substances known as such to the skilled person that on contact with compounds containing hydrogen groups are able to cleave off elemental or molecular hydrogen from these compounds. Suitable metals are, for instance, sodium, potassium, magnesium, calcium and zinc.

Suitable compounds containing hydrogen groups are all substances known as such to the skilled person that comprise at least one hydrogen function which is sufficiently acidic to release hydrogen in elemental or molecular form on contact with non-precious metal, such as, more particularly, compounds containing hydroxyl groups. Suitable compounds containing hydrogen groups are alcohols such as methanol, ethanol, n- and isopropanol, n-, sec- and tert-butanol, acids such as formic acid, acetic acid, malonic acid, citric acid or polyacrylic acid, and derivatives and copolymers of polyacrylic acid.

The process of the invention may optionally be carried out in a solvent or undiluted. Suitable solvents are, for example, alcohols such as methanol or ethanol, cyclic ethers such as tetrahydrofuran or dioxane, acyclic ethers such as tert-butyl methyl ether, tert-butyl ethyl ether, diethyl ether and diisopropyl ether, N,N-dialkyl amides of aliphatic carboxylic acids such as N,N-dimethylacetamide, N-alkyl lactams such as N-methylpyrrolidone, hydrocarbons such as pentane, and acids such as acetic acid. The reaction is preferably carried out without solvents. The hydrogenation of the invention may be carried out continuously or batchwise.

Suitable catalysts for the hydrogenation are precious metals such as ruthenium, rhodium, cobalt, nickel, palladium or platinum. Preference is given to ruthenium, rhodium, palladium and platinum. Particularly preferred are the transition metals platinum and palladium.

The hydrogenation of the alkene groups in the cyclohexanedimethanol derivative of the formulae 3a, 3b and/or 3c, for instance vinyl ether groups (R1 and/or R2=vinyl), takes place preferably at temperatures in the range from 20 to 250° C., more particularly 50 to 150° C., especially in the range from 80 to 100° C.

The hydrogenation takes place preferably under a hydrogen pressure of about 5 to 50 bar, more preferably a hydrogen pressure of 10 to 30 bar.

In one particular embodiment, the hydrogenation takes place at temperatures in the range from 20 to 100° C. and especially at about 20 to 40° C., with hydrogen (about 5 to 50 bar, preferably 10 to 30 bar hydrogen pressure).

The reaction times necessary for the hydrogenation are of course dependent conventionally on the reaction conditions or can be determined by routine methods.

The hydrogenation of the alkene groups in the cyclohexanedimethanol derivative of the formulae 3a, 3b and/or 3c, for instance vinyl ether groups (R1 and/or R2=vinyl), may be carried out for example as follows: for example, cyclohexanedimethanol monovinyl or divinyl ethers are placed in the autoclave with a catalyst, for instance palladium on aluminum oxide. The hydrogenation is carried out with thorough mixing at about 20 to 250° C., more particularly in the range from 50 to 150° C., especially in the range from 80 to 100° C. or in the range from about 20 to 100° C., preferably about 20 to 40° C., with hydrogen (about 5 to 50 bar, preferably 10 to 30 bar hydrogen pressure) for 5 to 20 hours, preferably 10 to 15 hours, the thorough mixing being brought about, for instance, by stirring at a high speed of, for example, 50 to 1000 rpm (as the size of the vessel goes down, a higher speed is required). After the end of hydrogen uptake, reaction is continued for one to 5 hours, which is followed by cooling and let down and also by removal of the catalyst by filtration. The purity of the product can be determined for instance by gas chromatography. There may optionally also be a subsequent distillation if products of higher purity are required.

The attainment of high fractions of the cis or trans isomer is typically not achieved, or not solely achieved, by the preparation methods of the invention, i.e. by alkenylation with an alkyne or by hydrogenation, since in these reactions there is generally no change in the stereoisomerism on the cyclohexyl ring, especially not when there are no substituents on the ring which are changed by a reaction. These fractional ratios ought therefore to be preferably already present in the starting material. The fractional ratios of cis isomer to trans isomer may also be set by separating the isomers, more particularly by distillative separation of the isomers.

A distillative separation of cis isomer and trans isomer may be carried out in analogy to known methods for the distillative separation of cis and trans isomers of cyclohexane derivatives, preferably by countercurrent distillation. The reflux ratio selected in this case is preferably in the range from 5:1 to 300:1, frequently in the range from 20:1 to 200:1, and more particularly in the range from 50:1 to 150:1. The distillation takes place preferably under reduced pressure, preferably a pressure in the range from 0.5 to 300 mbar, more particularly in the range from 2 to 50 mbar and especially in the range from 10 to 30 mbar. The distillation may be carried out in the apparatus typically employed for these purposes, preferably using a column, as for example a randomly packed column or a column with fixed internals, e.g. an ordered packing, or else a spinning band column, the latter being preferred for relatively small amounts. Preferred columns are those having at least 10, more particularly 10 to 200, theoretical plates.

Also possible is the subjection of cyclohexane derivatives of the formulae 3a, 3b and/or 3c in which one or both radicals R21 and/or R22 are C2- to C6-alkenyl to a hydrogenation which is selective with regard to the cis or trans isomer, followed by the separation of the unhydrogenated isomer from the hydrogenated isomer.

Methods for the production of cyclohexane derivatives with enriched cis or trans isomer by selective hydrogenation are known ("Efficient and Practical Arene Hydrogenation by Heterogeneous Catalysts under Mild Conditions", Authors: Maegawa, Tomohiro; Akashi, Akira; Yaguchi, Kiichiro; Iwasaki, Yohei; Shigetsura, Masahiro; Monguchi, Yasunari; Sajiki, Hironao; Chemistry—A European Journal (2009), 15(28), pages 6953-6963, S6953/1-S6953/85). Generally here the cis isomer is preferred. Ratios of about 85:15

(cis:trans) are disclosed. A cis-enriched mixture of this kind can be isomerized using heat and base, to give a cis-trans mixture of about 3:7 (U.S. Pat. No. 4,999,090). For the preparation of purer cis or trans isomers, enzymatic processes are known ("Lipase-mediated route to diastereo-pure tranexamic acid", Authors: Watanabe, Takashi; Hasegawa, Jin; Hiroya, Kou; Ogasawara, Kunio; in Chemical & Pharmaceutical Bulletin (1995), 43(3), 529-31).

Additionally found has been the combination of the two preparation processes of the invention, the alkenylation and the hydrogenation: found, accordingly, has been a process for preparing a cyclohexane derivative that comprises first preparing a cyclohexane derivative by the process described here, by alkenylation, followed by conversion into a different cyclohexane derivative by hydrogenation according to the process described here.

Found to be advantageous has been a process for preparing a cyclohexane derivative with a structure according to formula 1a, 1b or 1c (Formula 1a, 1b, 1c)

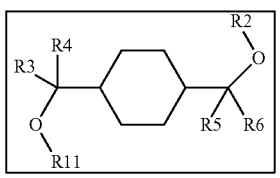

1a

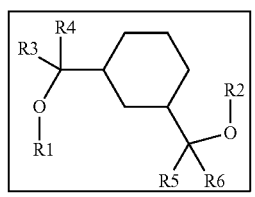

1b

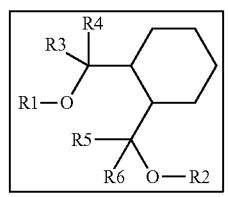

1c where the substituents on the cyclohexyl ring may be in cis or trans position to one another, and R1 is selected from the group consisting of Rc and hydrogen, and R2 is selected from the group consisting of Rc, and the radicals R3 to R6 independently of one another are selected from the group consisting of Rc and hydrogen, where Rc is a group consisting of C1- to C6-alkyl and C3- to C6-cycloalkyl, with the proviso that at least one radical from R1 and R2 is selected from C2- to C6-alkyl and that the summed total number of carbon atoms in all radicals R1 to R6 in the cyclohexane derivative of the formula 1 may only adopt a whole numerical value of 2 to 20, which comprises a) obtaining, in a first reaction step, a cyclohexane derivative with a structure according to formula 1aa, 1bb or 1cc (formula 1aa, 1bb, 1cc)

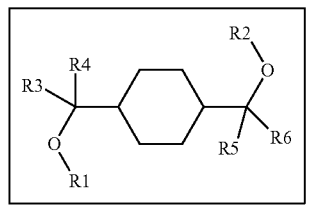

1a

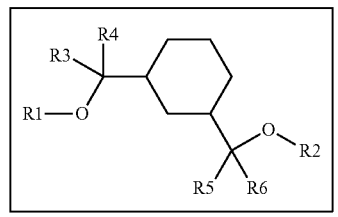

1b

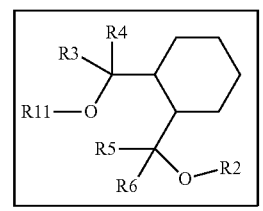

1c where the substituents on the cyclohexyl ring may be in cis or trans position to one another, and R1 and R2 independently of one another are selected from the group consisting of Re and hydrogen, and R3 to R6 independently of one another are selected from the group consisting of Rf and hydrogen, and where the group Rf consists of C1- to C6-alkyl, C3- to C6-cycloalkyl, C3- to C6-cycloalkenyl and C2- to C6-alkenyl and the group Re consists of C1- to C6-alkyl, C3- to C6-cycloalkyl and C2- to C6-alkenyl, with the provisos that at least one radical from R1 and R2 is selected from C2- to C6-alkenyl, and that the summed total number of carbon atoms in all radicals R1 to R6 in the cyclohexane derivative of the formula 1 may only adopt a whole numerical value of 2 to 20, by reaction of a cyclohexane derivative of the corresponding formula 2a, 2b or 2c (formula 2a, 2b, 2c)

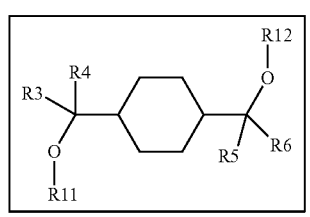

2a

-continued

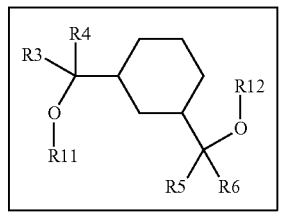
2b

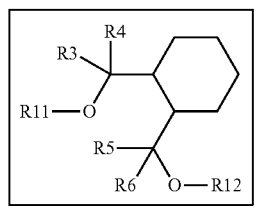
2c with at least one C2- to C6-alkyne,
where, in the cyclohexane derivative of the formulae 2a, 2b and/or 2c,
R3 to R6 independently of one another are selected from the group consisting of Rf and hydrogen,
R11 and R12 are hydrogen or a group Re, where at least one of the radicals, R11 and/or R12, is hydrogen,
where the groups Re and Rf consist of C1- to C6-alkyl, C2- to C6-alkenyl, C3- to C6-cycloalkyl and C3- to C6-cycloalkenyl,
where the radicals R11, R12, R3 to R6 and the alkyne are selected such that the summed total number of carbon atoms in all radicals R1 to R6 in the resultant compounds of the formulae 1a, 1b and/or 1c represents a whole numerical value of 2 to 20;
and
b) in a second reaction step, converting the cyclohexane derivative obtained in the first reaction step, by hydrogenation using hydrogen, into a corresponding cyclohexane derivative with a structure according to formula 1a, 1b or 1c.

The definition of the radicals R1 to R6 and also the radicals R11 and R12 is as defined above.

With regard to step a) in this process, the comments made above in relation to the reaction of the compound of the formulae 2a, 2b and/or 2c with the C2- to C6-alkyne with respect to reactants, products and reaction conditions apply in the same way. Similarly, with regard to step b) of this process, the comments made above in relation to the reaction of the compound of the formulae 3a, 3b and/or 3c with hydrogen in relation to reactants, products and reaction conditions apply in the same way.

This process is suitable more particularly for preparing a cyclohexane derivative of the formula 1a in which R1 and R2 are ethyl. In this case a compound of the general formula 2a in which R11 and R12 are hydrogen is reacted with ethyne to give a compound of the general formula 1aa in which R1 and R2 are vinyl, and this compound is hydrogenated with hydrogen. This process is specially suitable for preparing a cyclohexane derivative of the formula 1a in which R1 and R2 are ethyl and R3, R4, R5 and R6 are hydrogen. In this case a compound of the general formula 2a in which R11 and R12 are hydrogen and R3, R4, R5 and R6 are hydrogen is reacted with ethyne to give a compound of the general formula 1aa in which R1 and R2 are vinyl and R3, R4, R5 and R6 are hydrogen, and this compound is hydrogenated with hydrogen.

A particular advantage of the inventive combination of the two preparation processes of the invention is the possibility of a two-step reaction in direct succession, preferably without purification in between and more preferably in the same reaction vessel. The actual purification of the products to remove remnants of reaction materials such as catalyst and any residues of reactants takes place only after the end of the second reaction: one purification step is saved, implying a saving in time, energy, reactor vessels, reactor capacity, distillation time and distillation apparatus, and hence a massive cost saving.

If unreacted reactants from the first reaction step and/or the second reaction step are still present, they can easily be subjected again in their entirety, without separation, to the first, second or first and then second reaction steps. This too saves on further purification and hence costs.

It is merely advisable to separate off the volatile feedstocks—alkyne and/or hydrogen—before a further reaction is carried out. However, it is also possible not to separate off these feedstocks completely before a further reaction.

A particular advantage of the present invention arises from the volatility of the alkyne reagents, such as ethyne more particularly, and of the hydrogen reagent, which following the alkenylation can be removed completely or almost completely from the product by reducing the pressure in the reaction space and simply flushing with inert gas. As a result, it is possible to provide substances of high purity.

A high purity is also achieved in accordance with the invention by preparing the cyclohexane derivatives by the process of the invention of the direct sequence of alkenylation and subsequent hydrogenation without purification of the products in between.

In this way it is possible, for example, to obtain the monoethyl and diethyl ethers in very high purity from the monovinyl and divinyl ethers by reduction with hydrogen, and to obtain the monovinyl and divinyl ethers by alkenylating the diols with ethyne. The combination of these two reaction steps, as a direct sequence made up of alkynylation and subsequent hydrogenation, is one particularly preferred embodiment of the present invention.

A substance of "high purity" in the sense of this invention is a substance having a content of at least 97 percent, preferably at least 98 percent, more preferably at least 99 percent, very preferably at least 99.5 percent, and more particularly at least 99.7 percent, such as, for example, 99.9 or 99.95 percent and higher.

Particularly preferred, accordingly, is the preparation of monoethyl and diethyl ethers of the formulae 1aa, 1bb and 1cc by single or double vinylation of the monool or of the diol, respectively, of the formulae 2a, 2b and/or 2c with ethyne, and the subsequent direct reduction of the vinyl ethers obtained in the first step, using hydrogen, without purification of the products in between.

Another preparation method according to the invention is transalkenylation, in which an alkenyl group is transferred from an alkenyl donor compound to an alcohol. This is done by reacting a cyclohexane derivative of the general formula 2a, 2b or 2c, as defined above, with an alkenyl donor compound, i.e. a compound having at least one C2- to C6-alkenyl group, which is bonded via one of its olefinic C atoms to an oxygen atom or a nitrogen atom, with the C2- to C6-alkenyl group being more particularly a vinyl group. This reaction is shown diagrammatically in scheme 1 below, with the compound II being the alkenyl donor compound and the compound II the cyclohexane derivative of the general formula 2a, 2b or 2c:

Scheme 1:

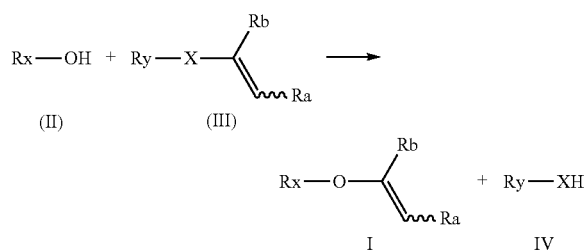

In scheme 1 Rx-O in formula I and formula II stands for a radical derived from a cyclohexane derivative of the formulae 2a, 2b and/or 2c. Ra and Rb stand independently of one another for hydrogen or C1-C4-alkyl, e.g. methyl, with the total number of carbons in Ra and Rb being 0, 1, 2, 3 or 4. More particularly Ra and Rb stand for hydrogen. In formula III and IV, respectively, Ry-X stands for a radical derived from an ether, ester, amide or lactam. More particularly X stands for O or N-Rz. Ry stands for example for aliphatic or cycloaliphatic hydrocarbon radical, e.g. for alkyl having preferably 2 to 6 C atoms, formyl or C1- to C6-alkylcarbonyl such as acetyl or propionyl, for a C1- to C6-alkylcarbonyl radical substituted by a group C(O)ORq or for a radical of the formula —$(CH_2CH_2O)_k$-Rq, in which k is 2 to 10 and Rq stands for a radical C(Rb)=CHRa. Rz stands for hydrogen or C1- to C4-alkyl or Rz, together with Ry and the nitrogen atom, forms an N-lactamyl radical having preferably 3, 4 or 5 C atoms as ring members, e.g. a pyrrolidin-2-on-1-yl radical.

Preferred alkenyl donor compounds of the formula III are isopropyl vinyl ether, isobutyl vinyl ether, diethylene glycol divinyl ether, vinyl formate, vinyl acetate, vinyl propionate, divinyl adipate, N-vinyl-2-pyrrolidone, N-vinyl-N-methylformamide and N-vinyl-N-methylacetamide.

The reaction of the cyclohexane derivative of the formulae 2a, 2b and/or 2c with the alkenyl donor compound may take place in analogy to processes known from the literature, of the kind described, for example, in WO 2011/139360, WO 2011/139361, EP 538685 and McKeon et al., Tetrahedron 28 (1972) pp. 227-283.

Generally speaking, the alkenyl donor compound is used in an at least stoichiometric amount, based on the cyclohexane derivative of the general formula 2a, 2b or 2c. The molar ratio of cyclohexane derivative of the general formula 2a, 2b or 2c to the alkenyl donor compound is situated preferably in the range from 1:10 to 1:1.

The reaction of the cyclohexane derivative of the general formula 2a, 2b or 2c with an alkenyl donor compound takes place typically in the presence of a catalyst. Suitable catalysts for this purpose are known from WO 2011/139360, WO 2011/139361, EP 538685 and McKeon et al., Tetrahedron 28 (1972) pp. 227-283. Suitable catalysts are transition metal salts, transition metal complexes, more particularly those of palladium, platinum, ruthenium, rhodium, iridium or mercury, more particularly palladium salts and palladium complexes, and also bases. Preference is given to transition metal complexes, more particularly those of the aforementioned transition metals, especially of palladium, with monodentate ligands, examples being pyridine, tri(C2- to C4-alkyl)phosphines or triphenylphosphine, or with chelate ligands, examples being N,N,N',N'-tetra(C1- to C4-alkyl)-C2- to C4-alkylenediamines such as N,N,N',N'-tetramethyl-1,2-ethanediamine, 2,2'-bipyridine and substituted 2,2'-bipyridine, phenanthroline and substituted phenanthroline, and also P,P,P',P'-tetraphenyl-1,2-diphosphinoethane. Particularly preferred are complexes of palladium with monodentate ligands or chelate ligands, more particularly complexes of palladium(III), e.g. diacetato complexes, more preferably complexes of palladium(III) with chelate ligands, especially with phenanthroline, substituted phenanthroline, N,N,N',N'-tetramethyl-1,2-ethanediamine, 2,2'-bipyridine or P,P,P',P'-tetraphenyl-1,2-diphosphinoethane, e.g. the corresponding diacetatopalladium(II) complexes with one of the aforementioned chelate ligands. Preferred bases are alkali metal and alkaline earth metal hydroxides, alkali metal and alkaline earth metal alkoxides and alkali metal and alkaline earth metal carbonates, and also tertiary amines such as triethylamine and pyridine bases such as dimethylaminopyridine. The catalyst is used typically in an amount of 0.01 to 10 mol %, more particularly in an amount of 0.05 to 5 mol % and especially in an amount of 0.1 to 1 mol %, based on the cyclohexane derivative of the formulae 2a, 2b and/or 2c.

In one preferred embodiment of the process, a cyclohexane derivative of the formulae 1aa, 1bb and/or 1cc is prepared by reacting a cyclohexane derivative of the general formulae 2a, 2b or 2c, as defined above, with an alkenyl donor compound and then subjecting it to a hydrogenation with hydrogen. This procedure is suitable more particularly for preparing a cyclohexane derivative of the formulae 1a in which R1 and R2 are ethyl, in which case a compound of the general formula 2a in which R11 and R12 are hydrogen is reacted with a vinyl donor compound, i.e. an alkenyl donor compound whose alkenyl group is a vinyl group, to give a compound of the general formula 1aa in which R1 and R2 are vinyl, and this compound is hydrogenated with hydrogen.

The alkenylation with an alkenyl donor compound, for instance the preparation of cyclohexanedimethanol mono- and divinyl ethers, can be carried out as follows:

In a flask rendered inert with argon, cyclohexanedimethanol is introduced with 3 equivalents of isobutyl vinyl ether and melted. The catalyst, for example phenanthrolinepalladium diacetate (e.g. in an amount of 0.01 to 1 mol %), is added and the mixture is heated at reflux (in the case of the stated substances, this corresponds to about 82° C.). After a reaction time of from about 2 to 10 hours, the reaction is ended, and cooling is carried out to room temperature. One possible purification is, for example, distillation using known columns and column packings if products of higher purity are desired.

A further preparation method according to the invention is transetherification: in this, a vinyl ether group is displaced by an aldehyde, which then cleaves off water and forms a new, different alkenyl ether group. For this, the aldehyde must have an abstractable hydrogen atom on the carbon atom adjacent to the carbonyl group.

Also encompassed by the present invention is the use of novel bis(hydroxymethyl)cyclohexanes which are prepared by customary ether syntheses known to the person skilled in the art: to prepare the bis(hydroxymethyl)cyclohexanes according to the invention, it is possible for example also to continue directly, for example, the preparation procedures from JP 11-071312 A, in the description paragraphs [0012] to [0026] and also the examples in paragraphs [0030] to [0087], from JP 11-029512 A1, paragraphs [0015] to [0071], from JP 11-035969 A, paragraphs [016] to [0018] and [0022] to [0038], and also in accordance with the general specialist knowledge, for example to give the corresponding diethers by following with a further etherification in accordance with Williamson, and other metal-catalyzed and metal-mediated reactions.

The substances according to the present invention have in particular advantageous sensory properties, in particular odor.

Thus, substances according to the invention have the following odors:

Compound A (formula 1 a: R1 is vinyl, R2 to R6 are hydrogen, cis/trans mixture with a cis/trans ratio of 30:70): pear, coumarin, fruity-floral, somewhat green Compound B (formula 1 a: R1 and R2 are vinyl, R3 to R6 are hydrogen, cis/trans mixture with a cis/trans ratio of 30:70): fruity-sweet, pear with coumarin notes Compound I (formula 1 a: R1 is ethyl, R2 is ethyl, R3 to R6 are hydrogen, cis/trans mixture with a cis/trans ratio of 30:70): green, watery, coumarin, somewhat ozone-like and distantly reminiscent of menthofuran Compound I-trans (formula 1 a: R1 is ethyl, R2 is ethyl, R3 to R6 are hydrogen, cis/trans mixture with trans fraction above 95%): weak, low-intensity odor towards green, coumarin, very slight ozone-like smell The resulting cis/trans mixtures smell less intensively than the mixtures which comprise a higher fraction of the cis compound. The pure cis compounds smell very intensively.

Surprisingly, mixtures which comprise high fractions of the trans compound have a less pronounced smell. In particular, the trans compound of structure I (structure "1-trans") has a less precise odor. Structure I-trans has exceptional dissolution properties, particularly for customary ingredients in fragrance-comprising preparations.

Intensive odor impressions are to be understood as meaning those properties of aroma chemicals which permit a precise perception even in very low gas-space concentrations. The intensity can be ascertained via a threshold-value determination. A threshold value is the concentration of a substance in the relevant gas space at which an odor impression can just still be perceived by a representative test panel, although it no longer has to be defined. The substance class known as probably one of the most odor-intensive, i.e. those with very low threshold values, are thiols, whose threshold value is in the ppb/cbm range. It is the aim of the search for new aroma chemicals to find substances with the lowest possible threshold value in order to permit the lowest possible use concentration. The closer one comes to this target, the more one talks of "intensive" odor substances or aroma chemicals.

"Advantageous sensory properties" is a hedonic expression which describes the niceness and preciseness of an odor impression conveyed by an aroma chemical.

"Niceness" and "preciseness" are terms which are familiar to the person skilled in the art, a perfumer. Niceness generally refers to a spontaneously brought about, positively perceived, pleasant sensory impression. However, "nice" does not have to be synonymous with "sweet". "Nice" can also describe the odor of musk or sandalwood.

"Preciseness" generally refers to a spontaneously brought about sensory impression which—for the same test panel—brings about a reproducibly identical reminder of something specific.

For example, a substance can have an odor which is spontaneously reminiscent of that of an "apple": the odor would then be precisely of "apples". If this apple odor were very pleasant because the odor is reminiscent, for example, of a sweet, fully ripe apple, the odor would be termed "nice". However, the odor of a typically tart apple can also be precise. If both reactions arise upon smelling the substance, in the example thus a nice and precise apple odor, then this substance has particularly advantageous sensory properties.

The term "exceptional dissolution properties" refers to the solubility and also the solubilization in the perfumery application, i.e. both in the perfume oil itself, and also in the application matrix, such as soaps, creams, deodorants and others.

"Exceptional" dissolution properties are present for example if virtually all customary substances which can be used in such formulations are soluble in the solvent. "Good" dissolution properties are present if virtually all important substances which are used in such formulations are soluble in this solvent. "Moderate" dissolution properties are present if only a small fraction of the important substances is soluble or dispersible. Such substances, their importance and also the testing of the solubility in solvents are known to the person skilled in the art.

Consequently, the intensively or precisely smelling substances of the present invention are suitable for use as fragrance. Suitable fields of application are all applications in which a certain odor is desired, whether it is to mask more unpleasant odors or to generate a certain odor or certain odor notes in a targeted manner.

Lesser or less precisely smelling substances according to the invention are likewise suitable for use as formulation auxiliaries for fragrance-containing preparations.

Typical fields of application are therefore in each case laundry and cleaning detergents, preparations of fragrances for the human or animal body, for rooms such as kitchens, wet rooms, automobiles or heavy goods vehicles, for real or artificial plants, for clothing, for shoes and shoe insoles, for items of furniture, for carpets, for air humidifiers and air fresheners, for cosmetics such as perfumes, ointments, creams, gels, shampoos, soaps and also powders, for foods and food supplements, and also for pharmaceuticals and medical devices such as bandages, stockings, diapers, sprays and insoles.

Preferred applications are in the field of detergents and cleaners, preparations of fragrances for the human or animal body, for rooms for clothing, for shoes and shoe insoles, for air humidifiers and air fresheners and for cosmetics such as perfumes. Particular preference is given to use in detergents and cleaners, and also in perfumes. Particular preference is given to the use in perfumes.

The substances according to the invention, in particular the more odor-intensive substances, can be used in known mixtures and compositions as individual substance or as a mixture of two or more substances according to the invention in the amounts customary for fragrances.

The substances according to the invention, in particular the low-intensity smelling substances, can be used in known mixtures and compositions as individual substances or as a mixture of two or more substances according to the invention in the amounts customary for formulation auxiliaries.

The cyclohexane derivatives of the formulae 1a, 1b and/or 1c for use in accordance with the invention as aroma substances have a so-called booster effect for other fragrances. They are therefore suitable as boosters for numerous other fragrances.

Booster effect means that the substances enhance and intensify, in perfumery formulations, the overall impression of the mixture. In the mint range, for example, it is known that menthyl methyl ether intensifies the perfumery or taste mixtures of peppermint oils and particularly in top notes brings about a considerably more intensive and more complex perception although the ether itself, being a pure substance, develops no particular intensive odor at all.

Booster effects are particularly desired when top-note-characterized applications are required in which the odor impression is to be conveyed particularly quickly and intensively, for example in deodorants, air fresheners or in the taste sector in chewing gums.

The substances according to the invention, especially in floral compositions and also in mint formulations, have such a booster effect.

To achieve such a booster effect in floral compositions or else in mint compositions, the compounds according to the invention are generally used in a fraction of 0.1-20% by weight of the total mixture, preferably 0.5 to 5%, with an amount of from 0.6 to 3% being particularly suitable.

The invention also includes odorant combinations which comprise at least one cyclohexane derivative for use in accordance with the invention and having a structure according to formula 1a, 1b or 1c, more particularly at least one of the cyclohexane derivatives said to be preferred and having a structure according to formula 1a, 1b or 1c, as component A, and also at least one further compound known as an odorant or aroma substance, as component B, such as, for example, one or more of the following compounds B1 to B11:

B1: methyl dihydrojasmonate (e.g. hedione),
B2: 4,6,6,7,8,8-hexamethyl-1,3,4,6,7,8-hexahydrocyclopenta[g]benzopyran (e.g. Galaxolide™),
B3: 2-methyl-3-(4-tert-butylphenyl)propanal (Lysmeral™),
B4: 2-methyl-3-(4-isopropylphenyl)propanal (cyclamenaldehyde),
B5: 2,6-dimethyl-7-octen-2-ol (dihydromyrcenol),
B6: 3,7-dimethyl-1,6-octadien-3-ol (linalool),
B7: 3,7-dimethyl-trans-2,6-octadien-1-ol (geraniol),
B8: 2,3,8,8-tetramethyl-1,2,3,4,5,6,7,8-octahydro-2-naphthalenyl methyl ketone (Iso E Superm),
B9: alpha-hexylcinnamaldehyde,
B10: 3,7-dimethyl-6-octen-1-ol (citronellol),
B11: alpha- or beta- or delta-damascone.

In one preferred embodiment an odorant combination of this kind comprises as component A at least one cyclohexane derivative for use in accordance with the invention and having a structure of formula 1a, more particularly a cyclohexane derivative of the formula 1a in which R3, R4, R5 and R6 are hydrogen, and especially a cyclohexane derivative of the formula 1a in which R3, R4, R5 and R6 are hydrogen and R1 and R2 are identical or different and independently of one another are C2- to C6-alkyl or C2 to C6-alkenyl, and also at least one of the abovementioned compounds B1 to B11. In one specific embodiment an odorant combination of this kind comprises as component A a cyclohexane derivative with a structure of formula 1a in which R3, R4, R5 and R6 are hydrogen and R1 and R2 are ethyl and also, as component B, at least one of the aforementioned compounds B1 to B11.

Suitable formulations of odor substances are, for example, the formulations disclosed in JP 11-071312 A, paragraphs [0090] to [0092]. The formulations from JP 11-035969 A, paragraphs [0039] to [0043] are also likewise suitable.

With the substances according to the invention, a booster effect is possible depending on the composition of the preparations.

Particular advantages of the substances found are the easy synthetic accessibility, in particular of the vinyl ethers, ethyl ethers, diethyl ethers, isopropenyl ethers, diisopropenyl ethers, isopropyl ethers and diisopropyl ethers, the lack of toxicity in particular of the diethyl ethers, isopropenyl ethers, diisopropenyl ethers, isopropyl ethers and diisopropyl ethers, and also the surprising solvent properties in particular of the diethyl ethers.

Of particular advantage are the low-intensity odor and the exceptional dissolution properties of trans-1,4-bis(ethoxymethyl)cyclohexane.

Furthermore, the fruity scent notes of the fragrances found are particularly advantageous.

"Fruity notes" are those odor impressions which give the complex sensory impression of ripe fruits.

Particular advantages of the preparation processes are the high purity of the products, which can be achieved very easily—virtually directly from the reaction vessel without complex separation processes. This is particularly important because even the lowest concentrations of a substance can have a strong influence on the odor and the toxicology.

These impurities are of particular importance when they have a low threshold value (see above) and can thus cause an incorrect note in the lowest concentrations. This often occurs when sulfur-containing or nitrogen-containing compounds are used in the synthesis of aroma chemicals.

The atom economy of the preparation processes is likewise advantageous: all of the atoms of the reactants used are found again in the product after the reaction. No atom is "squandered" as waste product. As a result, no by-product is produced which would have to be separated off. In particular, no salts are formed which have to be separated off by complex process steps such as filtration, decantation or centrifugation and, as a rule, have to be disposed of in an expensive or complex manner.

The processes according to the invention are accordingly particularly efficient and particularly cost-effective to carry out.

In particular, it was surprising that the monoethyl ether of 1,4-bis(hydroxymethyl)cyclohexane is odorless. This was completely unexpected in view of the prior art, in particular of the Japanese disclosures cited at the outset which also include this compound. In particular, this was also surprising since the monovinyl ether has a significant odor.

In particular the short-chain diethers, such as, in particular, the diethyl ether of 1,4-bis-(hydroxymethyl)cyclohexane, with particular emphasis the trans compound, have particularly good, virtually universal solvent properties for other fragrances and other customary ingredients in fragrance-comprising preparations such as, in particular, perfumes. Likewise these substances are toxicologically acceptable and, moreover, also have an unexpected, very high stability of the ether groups.

These toxicologically advantageous properties are naturally applicable in particular only for those substances which do not have an olefinic group directly on the oxygen of the ether function. Substances such as the vinyl ethers are naturally more reactive and are therefore also as a rule to be viewed more critically from a toxicological aspect.

The exceptional solvent properties and thus the suitability of the ethers of bis(hydroxymethyl)cyclohexanes, preferably of the short-chain diethers, particularly preferably of the diethyl ethers and very particularly preferably of the diethyl ether of 1,4-bis-(hydroxymethyl)cyclohexane as formulation auxiliary for fragrance-containing preparations, particularly in the field of laundry and cleaning detergents and of cosmetic preparations, were unknown and also completely unexpected on the basis of the cyclohexane derivatives and their properties known hitherto.

EXAMPLES

Compound A (cis/trans ratio 30:70)

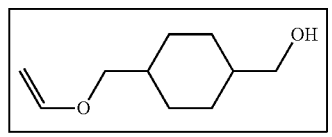

Compound B (cis/trans ratio 30:70)

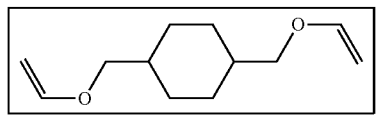

Compound I (cis/trans ratio 30:70)
Compound I-trans (trans/cis ratio >95:5)

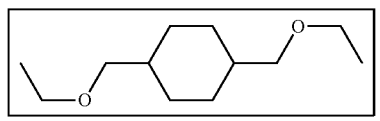

Synthesis Procedure for the Preparation of cyclohexanedimethanol divinyl ether (Compound B)

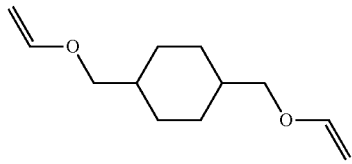

In a 20 L autoclave rendered inert with nitrogen, 10.8 kg of cyclohexanedimethanol were introduced together with 330 g of potassium hydroxide, melted and heated to a temperature of 160° C. with stirring. Acetylene was then injected to a total pressure of 20 bar and the amount of acetylene required to maintain the pressure was continuously topped up. After a reaction time of 9 h or a gas absorption >3000 L, the acetylene introduction was ended, and the apparatus was cooled to room temperature, decompressed and flushed with nitrogen. The crude product was analyzed by gas chromatography and comprised, according to area percent evaluation, 0.2% of starting material, 2.9% of cyclohexanedimethanol monovinyl ether and 93.9% of cyclohexanedimethanol divinyl ether. To purify the crude product, a part amount of 4 kg was distilled over a silver-plated 100 cm column, filled with 30 mm Sulzer DX packings, at a pressure of 10 mbar and a bottom temperature of 130° C. During this, 2.6 kg of divinyl ether were obtained in a purity of more than 98%, which corresponds to a distillation yield of 70%.

Synthesis Procedure for the Preparation of cyclohexanedimethanol mono- and divinyl ethers and Derivatives (Structures A and B)

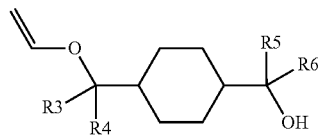

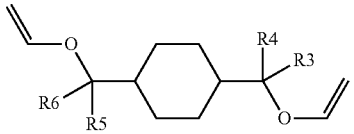

In a 20 L autoclave rendered inert with nitrogen, 10.8 kg of cyclohexanedimethanol were introduced together with 330 g of potassium hydroxide and 1500 g of isopropanol and heated to a temperature of 160° C. with stirring. Acetylene was then injected to a total pressure of 20 bar and the amount of acetylene required to maintain the pressure was continuously topped up. After a reaction time of about 3 h or a maximum gas absorption of 1800 L, the acetylene introduction was ended, and the apparatus was cooled to room temperature, decompressed and flushed with nitrogen.

The crude product was analyzed by gas chromatography and comprised, according to area percent evaluation, in the case of the compounds where R3 to R6 are hydrogen, 10.6% of starting material, 40.9% of cyclohexanedimethanol monovinyl ether, 37.4% of cyclohexanedimethanol divinyl ether. To purify the crude product, a part amount of 3.5 kg was distilled over a silver-plated 100 cm column filled with 30 mm Sulzer DX packings. After removing the isopropanol, this was carried out at a pressure of 10 mbar and a bottom temperature of 130-140° C. During this, 0.6 kg of monovinyl ether was obtained in a purity >98%, which corresponds to a distillation yield of 40%.

Synthesis of cyclohexanedimethanol monovinyl ether: Distillation

Used: 132 g

| Fraction | Amount | GC purity |
|---|---|---|
| 1 | 13.1 g | 96.5% |
| 2 | 44.3 g | 99.0% |
| 3 | 36.3 g | 99.2% |
| 4 | 19.0 g | 99.1% |
| Bottom | 21.8 g | 71.2% |

Cold trap: 0.6 g

The synthesis and purification of 1,2- and 1,3-cyclohexanedimethanol mono- and divinyl ethers and of substituted 1,2-, 1,3- and 1,4-cyclohexanedimethanol derivatives with at least one radical from R3 to R6 not being hydrogen can take place analogously; here, the corresponding molar amount of cyclohexanedimethanol or derivative is used as starting material.

Hydrogenation of cyclohexanedimethanol divinyl ether (Compound B) for the Preparation of cyclohexanedimethanol diethyl ether (Compound I/I-trans)

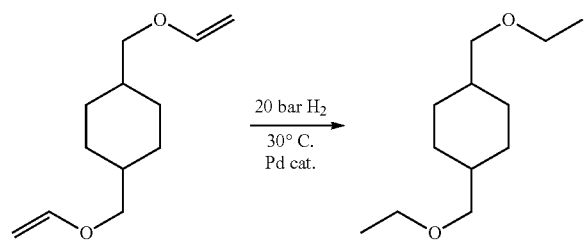

A 300 mL steel autoclave was filled with 150 g of cyclohexanedimethanol divinyl ether, 10 g of H0-22 catalyst (palladium on aluminum oxide) were placed in a suspended basket within the autoclave. The hydrogenation was carried out at 30° C. and 20 bar hydrogen for 12 hours with stirring (700 rpm). During this, 34.8 liters of hydrogen were injected in. The hydrogen absorption stopped after just 10 hours. The autoclave was cooled and decompressed, the product was filtered and gave 130 g of a clear liquid, the purity of which, according to GC, was 98.0%. By means of distillation, it was possible to obtain fractions with a purity of 99.7% (GC) (boiling point 98° C. at 4 mbar).
Synthesis of cyclohexanedimethanol diethyl ether: Distillation
Used: 130 g

| Fraction | Amount | GC purity |
|---|---|---|
| 1 | 9.5 g | 99.4% |
| 2 | 46.2 g | 99.6% |
| 3 | 42.7 g | 99.7% |
| 4 | 9.6 g | 99.7% |
| Bottom | 19.0 g | 87.4% |

Cold trap: 0.6 g

The synthesis and purification of 1,2- and 1,3-cyclohexanedimethanol mono- and divinyl ethers and of substituted 1,2-, 1,3- and 1,4-cyclohexanedimethanol derivatives with at least one radical from R3 to R6 not being hydrogen can take place analogously; here the corresponding molar amount of cyclohexanedimethanol or derivative is used as starting material.

The syntheses are known to the person skilled in the art from the prior art and/or can be carried out without further inventive skill in accordance with the known synthesis routes and also the synthesis routes disclosed here.
Further Synthesis Routes (for Procedure, See Instructions Above)
Synthesis Routes According to the Invention to Give Inventive diethyl and divinyl ethers of 1,2- and 1,3-cyclohexanedimethanol (According to the Invention):

Ethers of 1,2- and 1,3-cyclohexanedimethanol: vinyl, ethyl; cis-trans isomers; the divinyl ethers can be isolated in high purity Target structures:

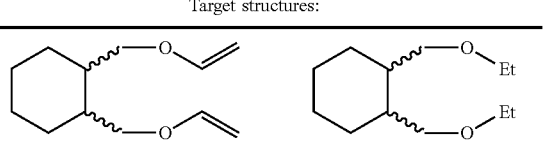

Ethers of 1,2- and 1,3-cyclohexanedimethanol: vinyl, ethyl; cis-trans isomers; the divinyl ethers can be isolated in high purity

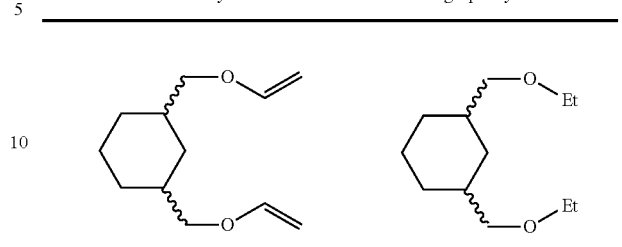

Synthesis routes:

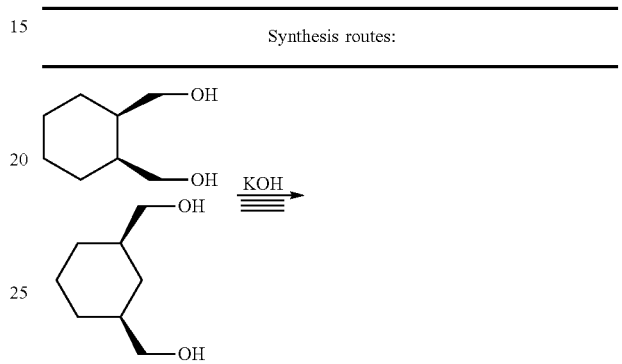

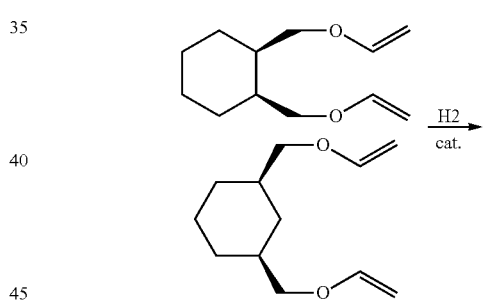

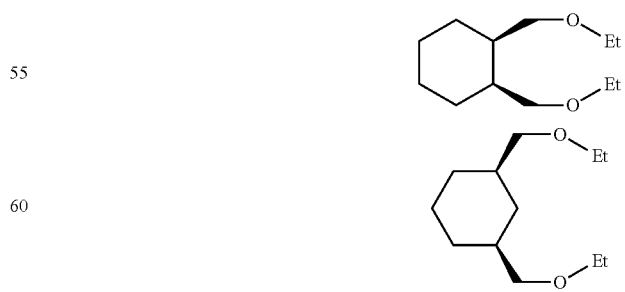

The preparation of the other alkenyl ethers with C3- to C6-alkenyl takes place analogously to this.

Synthesis Route to 1,4-cyclohexanedimethanol diethyl ether (Structures I and I-trans) (the Second Reaction Step is Comprised by the Present Invention):

cis-trans isomers of 1,4-cyclohexanedimethanol diethyl ether

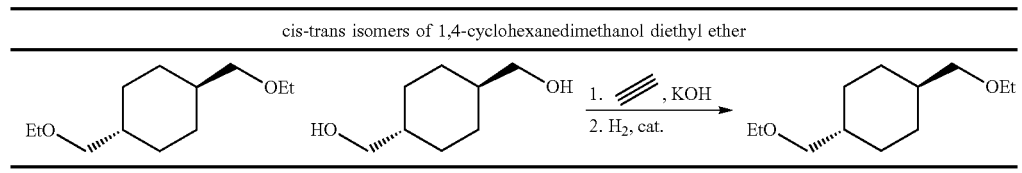

The preparation of the other inventive alkenyl ethers with C3- to C6-alkenyl takes place analogously to this.

Synthesis Routes to Inventive Non-Vinylic Ethers (Procedure According to General Specialist Knowledge):

Other ethers of 1,4-cyclohexanedimethanol; ethers of 1,2- and 1,3-cyclohexanedimethanol: analogous

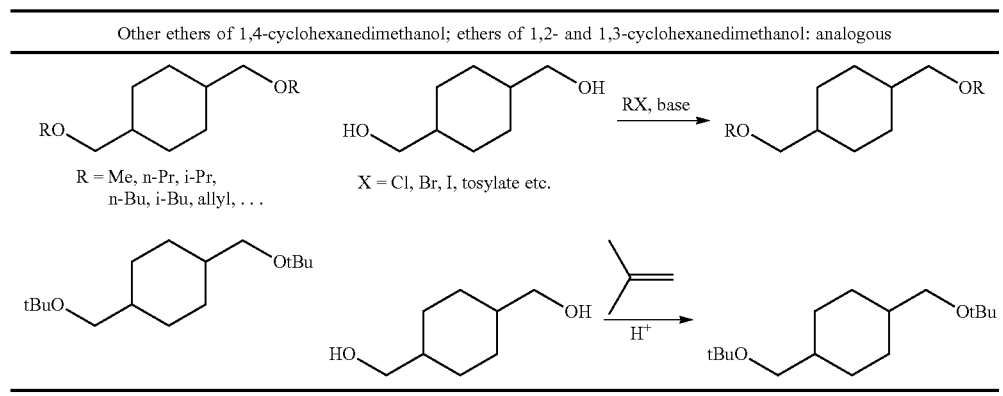

Synthesis of Inventive Trans-1,4-Cyclohexanedimethanol Diethyl Ether (Structure I-Trans) (Trans Fraction Greater than 95%)

1. Vinylation of trans-1,4-cyclohexanedimethanol

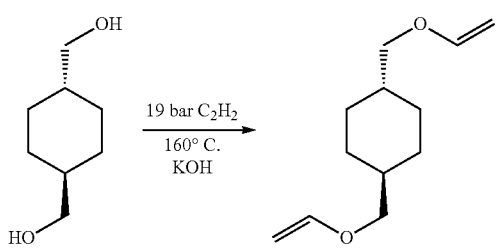

In a 250 mL flask, 120 g of trans-1,4-cyclohexanedimethanol were introduced together with 3.6 g of potassium hydroxide, melted and heated to a temperature of 180° C. with stirring. The mixture was poured warm into a 0.3 L autoclave rendered inert with nitrogen, and the temperature was adjusted to 160° C. Acetylene was then injected to a total pressure of 19 bar, and the amount of acetylene required to maintain the pressure was continuously topped up. After a reaction time of 23 h or a gas absorption of 33 L, the acetylene introduction was ended, and the apparatus was cooled to room temperature, decompressed and flushed with nitrogen. The crude product was analyzed by gas chromatography and comprised, according to area percent evaluation, 99.8% of trans-1,4-cyclohexanedimethanol divinyl ether and in each case <0.1% of starting material and monovinyl ether. For the purification, the crude product was distilled at a pressure of 1 mbar and a bottom temperature of 96° C. During this, 130 g of divinyl ether were obtained in a purity of more than 99%, which corresponds to a yield of 80%.

2. Hydrogenation of trans-1,4-cyclohexanedimethanol divinyl ether

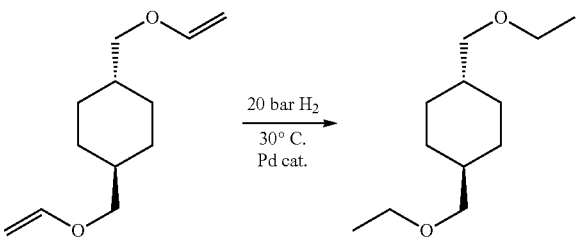

A 300 mL steel autoclave was filled with 120 g of cyclohexanedimethanol divinyl ether, and 8 g of H0-22 catalyst (palladium on aluminum oxide) were placed in a suspended basket within the autoclave. The hydrogenation was carried out at 30° C. and 20 bar hydrogen for 10 hours with stirring (700 rpm). During this, 27.8 liters of hydrogen were injected in. The autoclave was cooled and decompressed, and the product was filtered and gave 130 g of a clear liquid, the purity of which was 98.1% according to GC. By means of distillation, it was possible to obtain fractions with a purity of 99.9% (GC) (boiling point: 91° C. at 2 mbar).

3. Distillation

Used: 110 g

| Fraction | Amount | GC purity |
|---|---|---|
| 1 | 5.6 g | 99.36% |
| 2 | 7.0 g | 99.93% |
| 3 | 4.5 g | 99.94% |
| 4 | 54.2 g | 99.91% |
| 5 | 9.1 g | 99.68% |
| 6 | 19.8 g | 99.68% |
| 7 | 4.9 g | 99.10% |
| Bottom | 3.8 g | 67.74% |

Cold trap: 0.6 g

Synthesis of cis-1,2-cyclohexanedimethanol diethyl ether

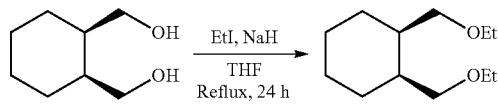 [SMILES: OC[C@@H]1CCCC[C@@H]1CO ; CCOC[C@H]1CCCC[C@H]1COCC]

Sodium hydride (2.5 g, 62 mmol) was introduced as 60% strength (% by weight) suspension in mineral oil in a 250 ml flask and washed twice with tetrahydrofuran (THF). Cis-1,2-cyclohexanedimethanol (9.0 g, 62 mmol), dissolved in 15 ml of THF, was added, and ethyl iodide (19.3 g, 124 mmol), dissolved in 15 ml of THF, was slowly added dropwise. The reaction mixture was heated at reflux for 24 hours. After cooling, 90 ml of acetic ester and 15 ml of water were added. The organic phase was washed three times with 50 ml of saturated sodium chloride solution. The organic phase was then dried over sodium sulfate and purified by distillation. This gave 10.6 g of a pale yellow liquid.

The product was analyzed by gas chromatography and comprised, according to area percent evaluation, 91% cis-1,2-cyclohexanedimethanol diethyl ether, 5% monoethyl ether, and other impurities, which in each case correspond to less than 1%. This corresponds to a yield of about 78%.

Purification takes place by distillation analogously to the preceding examples.

The invention claimed is:

1. A cyclohexane derivative with a structure according to formula 1c

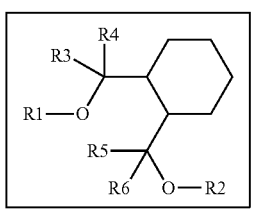

1c wherein the substituents on the cyclohexyl ring may be in cis or trans position to one another, and R1 to R6 independently of one another are selected from the group consisting of $C_2$-$C_6$-alkyl, $C_3$-$C_6$-cycloalkyl, $C_3$-$C_6$-cycloalkenyl, $C_2$-$C_6$-alkenyl and hydrogen, and R1 and R2 are not hydrogen, with the proviso that the summed total number of the carbon atoms in all radicals R1 to R6 is only a whole numerical value up to 20.

2. The cyclohexane derivative according to claim 1, wherein the cyclohexane derivative has a cis/trans ratio of at least 70:30.

3. The cyclohexane derivative according to claim 1, wherein the cyclohexane derivative has a trans/cis ratio of at least 70:30.

4. The cyclohexane derivative according to claim 1, wherein the cyclohexane derivative is 1,2-bis(ethoxymethyl)cyclohexane or 1,2-bis(vinyloxymethyl)cyclohexane.

5. A fragrance, flavor, or formulation auxiliary comprising a cyclohexane derivative with a structure according to formula 1c

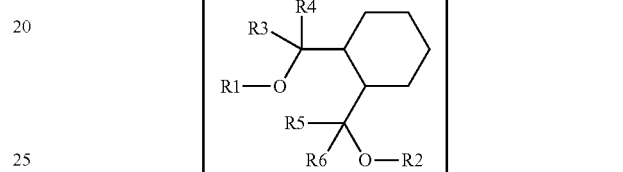

1c wherein the substituents on the cyclohexyl ring may be in cis or trans position to one another, and R1 to R6 independently of one another are selected from the group consisting of $C_1$-$C_6$-alkyl, $C_3$-$C_6$-cycloalkyl, $C_3$-$C_6$-cycloalkenyl, $C_2$-$C_6$-alkenyl and hydrogen, and at least one radical from R1 and R2 is not hydrogen, with the proviso that the summed total number of the carbon atoms in all radicals R1 to R6 is only a whole numerical value up to 20.

6. A composition comprising the fragrance, flavor, or formulation auxiliary according to claim 5, wherein the composition is a detergent, cosmetic preparation, fragranced hygiene article, food, food supplement, perfume, pharmaceutical preparation, or crop protection composition.

7. A formulating agent in a preparation comprising the fragrance, flavor, or formulation auxiliary according to claim 5.

8. The fragrance, flavor, or formulation auxiliary according to claim 5, wherein R1 and R2 are $C_1$-$C_4$-alkyl.

9. The fragrance, flavor, or formulation auxiliary according to claim 5, wherein R3, R4, R5, and R6, are hydrogen or methyl.

10. The fragrance, flavor, or formulation auxiliary according to claim 5, wherein R1 and R2 have the same definition.

11. The fragrance, flavor, or formulation auxiliary according to claim 5, wherein R1 and R2 are ethyl and R3 to R6 are hydrogen.

12. The fragrance, flavor, or formulation auxiliary according to claim 5, wherein the cyclohexane derivative is 1,2-bis(ethoxymethyl)cyclohexane or 1,2-bis(vinyloxymethyl)cyclohexane.

13. The fragrance, flavor, or formulation auxiliary according to claim 5, wherein the cis/trans ratio has a value of at least 70:30.

14. The fragrance, flavor, or formulation auxiliary according to claim 5, wherein the trans/cis ratio has a value of at least 70:30.

15. A process for preparing a cyclohexane derivative with a structure according to formula 1c

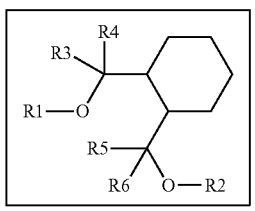

1c

R1 and R2 independently of one another are selected from the group consisting of Rb and hydrogen,
R3 to R6 independently of one another are selected from the group consisting of Ra and hydrogen,
Ra is $C_1$- to $C_6$-alkyl, $C_3$- to $C_6$-cycloalkyl, $C_3$- to $C_6$-cycloalkenyl, or $C_2$- to $C_6$-alkenyl, and
Rb is $C_1$- to $C_6$-alkyl, $C_3$- to $C_6$-cycloalkyl or $C_2$- to $C_6$-alkenyl,
with the proviso that at least one radical from R1 and R2 is $C_2$-$C_6$-alkenyl;
said process comprising
reacting a cyclohexane derivative of the corresponding formula 2c

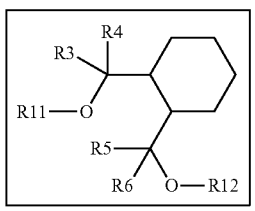

2c with at least one $C_2$-$C_6$-alkyne to obtain the cyclohexane derivative of the formula 1c,
wherein, in the cyclohexane derivative of the formula 2c,
R3 to R6 independently of one another are selected from the group consisting of Ra and hydrogen,
R11 and R12 are hydrogen or a group Rd, wherein at least one of the radicals, R11 and/or R12, is hydrogen,
Ra is $C_1$-$C_6$-alkyl, $C_3$-$C_6$-cycloalkyl, $C_3$-$C_6$-cycloalkenyl or $C_2$-$C_6$-alkenyl, and
Rd is $C_1$-$C_6$-alkyl, $C_3$-$C_6$-cycloalkyl or $C_2$-$C_6$-alkenyl,
wherein the radicals R11, R12, R3 to R6 and the $C_2$-$C_6$-alkyne are selected such that the summed total number of carbon atoms in all radicals R1 to R6 in the resultant compounds of the formula 1c, respectively, is a whole numerical value from 2 to 20,
and wherein the cyclohexane derivative of the formula 1c is obtained,
in which R1 is selected from $C_2$-$C_6$-alkenyl if R11 is hydrogen, and
in which R2 is selected from $C_2$-$C_6$-alkenyl if R12 is hydrogen.

16. The process according to claim 15, wherein in the cyclohexane derivative of the formula 1c, the radicals R1 and R2 are $C_2$-$C_6$-alkenyl.

17. The process according to claim 15, wherein R1 is the same as R2.

18. The process according to claim 15, wherein the $C_2$-$C_6$-alkyne is ethyne.

19. A process for preparing a cyclohexane derivative with a structure according to formula 1c

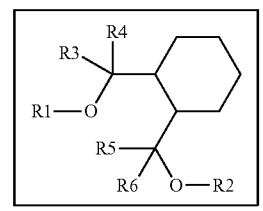

1c

R1 is selected from the group consisting of Rc and hydrogen,
R2 is Rc,
R3 to R6, independently of one another, are selected from the group consisting of Rc and hydrogen, and
Rc is $C_1$-$C_6$-alkyl or $C_3$-$C_6$-cycloalkyl,
with the proviso that at least one of the radicals, R1 and/or R2, is $C_2$-$C_6$-alkyl or $C_3$-$C_6$-cycloalkyl;
said process comprising
hydrogenating a cyclohexane derivative of the formula 3c

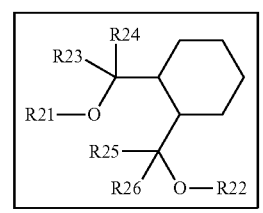

3c with hydrogen to obtain the cyclohexane derivative of the formula 1c,
wherein, in the further cyclohexane derivative of the formula 3c,
R21 is selected from the group consisting of Ra and hydrogen,
R22 is Ra,
R23 to R26 independently of one another are selected from the group consisting of Ra and hydrogen,
Ra is $C_1$-$C_6$-alkyl, $C_3$-$C_6$-cycloalkyl, $C_3$-$C_6$-cycloalkenyl or $C_2$-$C_6$-alkenyl, and
at least one of the radicals R21 to R26 is $C_3$-$C_6$-cycloalkenyl or $C_2$-$C_6$-alkenyl,
wherein the radicals R21 to R26 are selected such that the summed total number of carbon atoms in all radicals R21 to R26 may only represent a whole numerical value from 2 to 20.

20. The process according to claim 19, wherein at least one radical from R21 and R22 is $C_2$-$C_6$-alkenyl.

21. The process according to claim 19, wherein, in the cyclohexane derivative of the formula 3c, R21 is hydrogen.

22. The process according to claim 20, wherein, in the cyclohexane derivative of the formula 3c, R21 and R22 independently of one another are $C_2$-$C_6$-alkenyl.

23. The process according to claim 19, wherein, in the cyclohexane derivative of the formula 3c, R21 is the same as R22.

24. The process according to claim 19, wherein the $C_2$-$C_6$-alkenyl group is vinyl.

25. A process for preparing a cyclohexane derivative with a structure according to formula 1c,

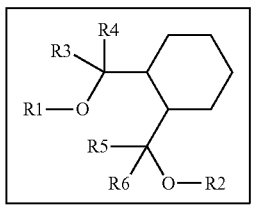

1c

R1 is selected from the group consisting of hydrogen and Rc,
R2 is selected from the group consisting of hydrogen and Rc,
R3 to R6 independently of one another are selected from the group consisting of Rc and hydrogen
Rc is $C_1$-$C_6$-alkyl or $C_3$-$C_6$-cycloalkyl,
with the proviso that at least one of R1 and R2 is $C_2$-$C_6$-alkyl,
said process comprising:
reacting a cyclohexane derivative of the corresponding formula 2c

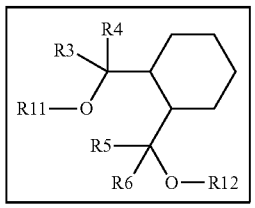

2c with at least one $C_2$-$C_6$-alkyne,
wherein, in the second cyclohexane derivatives of the formula 2c,
R3 to R6 independently of one another are selected from the group consisting of Rf and hydrogen,
R11 and R12 are hydrogen or a group Re, wherein at least one of the radicals R11 and/or R12 is hydrogen,
Re and Rf are $C_1$-$C_6$-alkyl, $C_2$-$C_6$-alkenyl, $C_3$-$C_6$-cycloalkyl or $C_3$-$C_6$-cycloalkenyl,
R11, R12, R3 to R6 and the $C_2$-$C_6$-alkyne are selected such that the summed total number of carbon atoms in all radicals R1 to R6 in the resultant compounds of the formula 1c represents a whole numerical value from 2 to 20,
wherein a cyclohexane derivative of the formula 1cc is obtained,

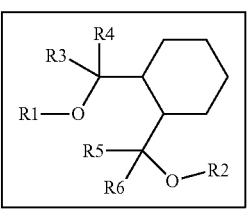

1cc wherein
R1 and R2 are hydrogen or a group Re,
R1 is $C_2$-$C_6$-alkenyl if R11 is hydrogen,
R2 is $C_2$-$C_6$-alkenyl if R12 is hydrogen,
R3 to R6 independently of one another are selected from the group consisting of Rf and hydrogen,
the summed total number of carbon atoms in all radicals R1, R2, R3, R4, R5 and R6 represents a whole numerical value from 2 to 20, and
hydrogenating the cyclohexane derivative of the formula 1cc with hydrogen.

26. The process according to claim 25 wherein R1 and R2 are ethyl, wherein a compound of the general formula 2c in which R11 and R12 are hydrogen is reacted with ethyne to give a compound of the general formula 1cc in which R1 and R2 are vinyl, and wherein said compound is hydrogenated with hydrogen.

27. A process for preparing a cyclohexane derivative of the formula 1cc,

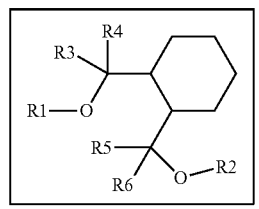

1cc wherein the substituents on the cyclohexyl ring may be in cis or trans position to one another, and
R1 and R2 are hydrogen or a group Re, wherein at least one of R1 and R2 is $C_2$-$C_6$-alkenyl,
R3 to R6 independently of one another are selected from the group consisting of Rf and hydrogen,
Re and Rf are $C_1$-$C_6$-alkyl, $C_2$-$C_6$-alkenyl, $C_3$-$C_6$-cycloalkyl or $C_3$-$C_6$-cycloalkenyl, and
the summed total number of carbon atoms in all radicals R1, R2, R3, R4, R5 and R6 of the formula 1cc, respectively, represents a whole numerical value from 2 to 20,
said process comprising:
reacting a cyclohexane derivative of the corresponding formula 2c

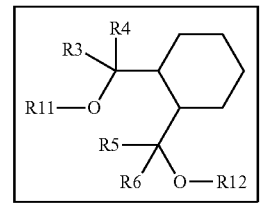

2c with at least one $C_2$-$C_6$-alkenyl donor compound in the presence of a transition metal catalyst or a base,
wherein, in the cyclohexane derivative of the formula 2c,
R3 to R6 independently of one another are selected from the group consisting of Rf and hydrogen,
R11 and R12 are hydrogen or a group Re, wherein at least one of R11 and R12 is hydrogen,
Re and Rf are $C_1$-$C_6$-alkyl, $C_2$-$C_6$-alkenyl, $C_3$-$C_6$-cycloalkyl or $C_3$-$C_6$-cycloalkenyl,
R11, R12, R3 to R6 and the alkyne are selected such that the summed total number of carbon atoms in all radicals R1 to R6 in the resultant compounds of the formula 1c represents a whole numerical value from 2 to 20, to give a cyclohexane derivative of the formula 1cc,
wherein R1 is $C_2$-$C_6$-alkenyl if R11 is hydrogen, and R2 is $C_2$-$C_6$-alkenyl if R12 is hydrogen.

28. The process according to claim 27, wherein the alkenyl donor compound is a compound of the general formula III

(III)

wherein
Ra and Rb independently of one another are hydrogen or $C_1$-$C_4$-alkyl, the total carbon number in Ra and Rb being 0, 1, 2, 3 or 4;
X is O or N-Rz;
Ry is $C_2$-$C_6$-alkyl, formyl, $C_1$-$C_6$-alkylcarbonyl, a $C_1$-$C_6$-alkylcarbonyl substituted by a group C(O)ORq, or a radical of the formula —$(CH_2CH_2O)_k$-Rq, in which k is 2 to 10;
Rz is hydrogen or $C_1$-$C_4$-alkyl, or Rz, together with Ry and the nitrogen atom, forms an N-lactamyl radical, and
Rq is a radical C(Rb)=CHRa.

29. A process for preparing a cyclohexane derivative with a structure according to formula 1c,

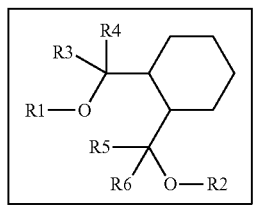

1c

R1 is selected from the group consisting of hydrogen and Rc,
R2 is selected from the group consisting of hydrogen and Rc,
R3 to R6 independently of one another are selected from the group consisting of Rc and hydrogen,
Rc is $C_1$-$C_6$-alkyl or $C_3$-$C_6$-cycloalkyl,
with the proviso that at least one radical from R1 and R2 is $C_2$-$C_6$-alkyl;
said process comprising
reacting a cyclohexane derivative of the corresponding formula 2c

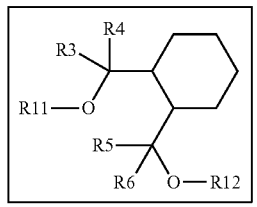

2c with at least one $C_2$-$C_6$-alkenyl donor compound in the presence of a transition metal catalyst or a base, wherein, in the cyclohexane derivative of the formula 2c,
R3 to R6 independently of one another are selected from the group consisting of Rf and hydrogen,
R11 and R12 are hydrogen or a group Re, wherein at least one of R11 and R12 is hydrogen,
Re and Rf are $C_1$-$C_6$-alkyl, $C_2$-$C_6$-alkenyl, $C_3$-$C_6$-cycloalkyl or $C_3$-$C_6$-cycloalkenyl,
R11, R12, R3 to R6 and the alkyne are selected such that the summed total number of carbon atoms in all radicals R1 to R6 in the resultant compounds of the formula 1c represents a whole numerical value from 2 to 20,
to give a cyclohexane derivative of the formula 1cc

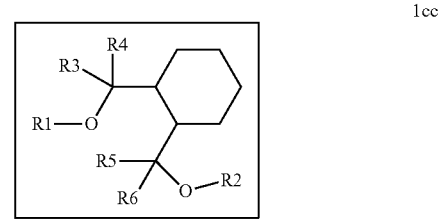

1cc wherein R1 is $C_2$-$C_6$-alkenyl if R11 is hydrogen, and R2 is $C_2$-$C_6$-alkenyl if R12 is hydrogen, and
hydrogenating the cyclohexane derivative of the formula 1cc with hydrogen.

30. The process according to claim 29, wherein R1 and R2 are ethyl, said process comprising
reacting a compound of the general formula 2c

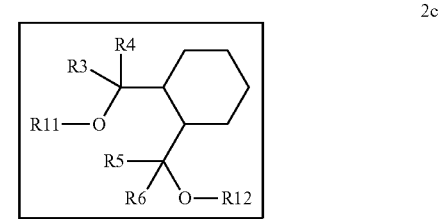

2c in which R11 and R12 are hydrogen with at least one $C_2$-$C_6$-alkenyl donor compound in the presence of a transition metal catalyst or a base,
wherein, in the compound of the general formula 2c,
R3 to R6 independently of one another are selected from the group consisting of Rf and hydrogen,
R11 and R12 are hydrogen or a group Re, wherein at least one of R11 and R12 is hydrogen,
wherein Re and Rf are selected from the group consisting of $C_1$-$C_6$-alkyl, $C_2$-$C_6$-alkenyl, $C_3$-$C_6$-cycloalkyl and $C_3$-$C_6$-cycloalkenyl,
wherein the radicals R11, R12, R3 to R6 and the alkyne are selected such that the summed total number of carbon atoms in all radicals R1 to R6 in the resultant cyclohexane derivative of the formula 1a represents a whole numerical value from 2 to 20, to give a compound of the general formula 1cc

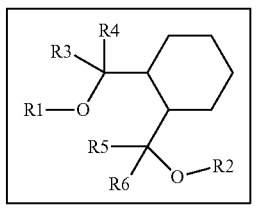

1cc in which R1 and R2 are vinyl, and
hydrogenating the compound of the general formula 1cc with hydrogen.

31. A method of imparting or modifying a scent or a flavor to a composition comprising incorporating a cyclohexane derivative into a composition in an amount that imparts or modifies the scent or the flavor of the composition, wherein the cyclohexane derivative has a structure according to formula 1c

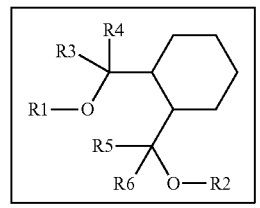

1c wherein the substituents on the cyclohexyl ring may be in cis or trans position to one another, and
R3 to R6 are hydrogen, and R1 and R2 independently of one another are selected from the group consisting of $C_2$-$C_6$-alkyl, $C_5$-alkenyl, $C_3$-$C_6$-cycloalkenyl and $C_3$-$C_6$-cycloalkyl, or
at least one radical from R3 to R6 is not methyl or hydrogen, and the other radicals R3 to R6 independently of one another are selected from the group consisting of $C_1$-$C_6$-alkyl, $C_3$-$C_6$-cycloalkyl, $C_3$-$C_6$-cycloalkenyl, $C_2$-$C_6$-alkenyl and hydrogen, and R1 and R2 independently of one another are selected from the group consisting of $C_1$-$C_6$-alkyl, $C_2$-$C_5$-alkenyl, $C_3$-$C_6$-cycloalkenyl and $C_3$-$C_6$-cycloalkyl, or
at least one radical from R1 and R2 is not methyl or ethyl, R3 and R4 are methyl, R5 and R6 are hydrogen, and also R1 and R2 independently of one another are selected from the group consisting of $C_1$-$C_6$-alkyl, $C_3$-$C_6$-cycloalkyl, $C_3$-$C_6$-cycloalkenyl, and $C_2$-$C_6$-alkenyl, or
R1 and R2 independently of one another are selected from the group consisting of $C_1$-$C_6$-alkyl, $C_3$-$C_6$-cycloalkyl, $C_3$-$C_6$-cycloalkenyl, and $C_2$-$C_6$-alkenyl, and at least one radical from R3 to R6 is not hydrogen, with the exception of compounds of the formula 1c in which R1 and R2 are methyl or ethyl and at the same time R3 and R4 are each methyl and R5 and R6 are each hydrogen,
and if R1 is hydrogen, R2 is not methyl, $C_4$-alkyl, or vinyl,
with the proviso that the summed total number of the carbon atoms in all radicals R1 to R6 is only a whole numerical value from 2 to 20.

32. The method according to claim 31, wherein the cyclohexane derivative is selected from 1,2-bis(ethoxymethyl)cyclohexane and 1,2-bis(tert-butoxymethyl)cyclohexane.

33. The method according to claim 31, wherein the cyclohexane derivative is selected from the group consisting of compounds of the formula 1c having a cis/trans ratio of at least 70:30.

34. The method according to claim 31, wherein the cyclohexane derivative is selected from the group consisting of compounds of the formula 1c having a trans/cis ratio of at least 70:30.

35. A fragrance dispenser comprising a composition comprising the fragrance, flavor, or formulation auxiliary according to claim 5.

* * * * *